United States Patent
Khader

(10) Patent No.: US 12,402,851 B2
(45) Date of Patent: Sep. 2, 2025

(54) SYSTEMS AND METHODS FOR ANATOMICAL FEATURE DETERMINATION

(71) Applicant: Edwards Lifesciences Corporation, Irvine, CA (US)

(72) Inventor: Yara Khader, Nazareth-Illit (IL)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 391 days.

(21) Appl. No.: 17/816,204

(22) Filed: Jul. 29, 2022

(65) Prior Publication Data
US 2022/0361835 A1 Nov. 17, 2022

Related U.S. Application Data

(63) Continuation of application No. PCT/US2021/016139, filed on Feb. 2, 2021.
(Continued)

(51) Int. Cl.
*A61B 6/00* (2024.01)
*A61B 6/03* (2006.01)
(Continued)

(52) U.S. Cl.
CPC ............ *A61B 6/5217* (2013.01); *A61B 6/032* (2013.01); *A61B 6/503* (2013.01); *G06T 7/74* (2017.01); *G16H 30/40* (2018.01); *G06T 2207/30048* (2013.01); *G06T 2207/30052* (2013.01); *G06T 2207/30101* (2013.01)

(58) Field of Classification Search
CPC ............ A61B 2018/00369; G06T 2207/30048
See application file for complete search history.

(56) References Cited

U.S. PATENT DOCUMENTS

| | | | |
|---|---|---|---|
| 8,560,968 B1* | 10/2013 | Nair | G16H 40/63 715/810 |
| 2013/0023985 A1* | 1/2013 | Khairkhahan | A61F 2/2463 623/2.38 |

(Continued)

FOREIGN PATENT DOCUMENTS

WO WO-2016038169 A1 3/2016

OTHER PUBLICATIONS

Takaoka H., et al., "Utility of Computed Tomography in Cases of Aortic Valve Stenosis Before and After Transcatheter Aortic Valve Implantation," Cardiovascular Intervention and Therapeutics, Springer Japan, Tokyo, Sep. 11, 2019, vol. 35, No. 1, pp. 72-84, DOI: http://dx.doi.org/10.1007/s12928-019-00618-5, ISSN 1868-4300, XP036978312.

*Primary Examiner* — Wen W Huang
(74) *Attorney, Agent, or Firm* — Chang & Hale LLP; Joel B. German

(57) ABSTRACT

Techniques for determining a position of a native leaflet can include identifying a position of a mineral formation on the native leaflet before implantation of a prosthetic valve and analyzing an image representing the prosthetic valve implanted within the cardiac vessel. The analysis can identify a position of the mineral formation within the cardiac vessel after the prosthetic valve is implanted. Based on the position of the mineral formation on the native leaflet before implantation of the prosthetic valve and the position of the mineral formation within the cardiac vessel, a position of the native leaflet within the cardiac vessel can be determined.

19 Claims, 12 Drawing Sheets

Related U.S. Application Data

(60) Provisional application No. 62/970,110, filed on Feb. 4, 2020.

(51) Int. Cl.
  *A61B 6/50* (2024.01)
  *G06T 7/73* (2017.01)
  *G16H 30/40* (2018.01)

(56) References Cited

U.S. PATENT DOCUMENTS

| | | | | |
|---|---|---|---|---|
| 2013/0155064 | A1* | 6/2013 | Grbic | G06T 7/11 345/420 |
| 2014/0163592 | A1* | 6/2014 | Hawkins | A61B 17/22012 606/159 |
| 2016/0038246 | A1* | 2/2016 | Wang | A61B 34/10 600/587 |
| 2016/0166332 | A1* | 6/2016 | Wang | A61B 34/10 703/11 |
| 2017/0301096 | A1* | 10/2017 | Weese | G06T 7/12 |
| 2019/0298450 | A1* | 10/2019 | Dasi | G16H 50/50 |
| 2020/0197033 | A1* | 6/2020 | Pasquino | A61B 17/221 |

* cited by examiner

SYSTEMS AND METHODS FOR ANATOMICAL FEATURE DETERMINATION

CROSS-REFERENCE TO RELATED APPLICATIONS

This application is a continuation of PCT Patent Application No. PCT/US2021/016139 filed on Feb. 2, 2021, which application claims the benefit of and priority to U.S. Provisional Application No. 62/970,110, filed Feb. 4, 2020, each of these applications being incorporated herein by reference it its entirety.

BACKGROUND

Field

The present disclosure relates to the field of medical devices and procedures.

Description of the Related Art

Aortic valve calcification occurs when calcium deposits form on the aortic valve in the heart. The calcium deposits can cause the aortic valve to narrow at the opening and/or become stiff. When the calcification becomes severe, the aortic valve fails to open and close properly, which affects blood flow through the valve, a condition called aortic valve stenosis. Certain cases of aortic valve calcification or stenosis require the aortic valve to be replaced with a prosthetic valve.

SUMMARY

Described herein are one or more methods and/or systems anatomical feature determination. In some aspects, the present disclosure relates to methods and systems for determining access for an anatomical feature based on an analysis of one or more images representing a mineral deposit.

In some embodiments, the present disclosure relates to a method for determining a position of a native leaflet. The method can comprise obtaining a pre-procedure image representing a native valve within a cardiac vessel and analyzing the pre-procedure image to determine a position of a mineral deposit on a native leaflet of the native valve. The method can also comprise obtaining, by control circuitry, a post-procedure image representing a prosthetic valve implanted at the native valve and analyzing the post-procedure image to identify a position of the mineral deposit within the cardiac vessel. Further, the method can comprise determining, by the control circuitry, a position of the native leaflet within the cardiac vessel. The position of the native leaflet can be determined based at least in part on the position of the mineral deposit on the native leaflet and the position of the mineral deposit within the cardiac vessel. In some implementations, the native valve comprises the aortic valve and the cardiac vessel comprises the aorta.

In some implementations, the method further comprises, based at least in part on the position of the native leaflet within the cardiac vessel, determining access to a fluid vessel associated with the cardiac vessel. In some embodiments, the method further comprises, based at least in part on the analysis of the post-procedure image, identifying a position of at least a portion of the prosthetic valve within the cardiac vessel. The determining access to the fluid vessel can be based at least in part on the position of at least the portion of the prosthetic valve within the cardiac vessel.

Moreover, in some embodiments, the method further comprises, based at least in part on the analysis of the pre-procedure image, identifying a position of coapt leaflets within the cardiac vessel, based at least in part on the position of the coapt leaflets, determining an end of the native leaflet, and determining a distance between the end of the native leaflet and the mineral deposit. The determining access to the fluid vessel can be based at least in part on the distance between the end of the native leaflet and the mineral deposit.

In some implementations, the analyzing the pre-procedure image to identify the position of the mineral deposit on the native leaflet can comprise generating user interface data representing the pre-procedure image, providing the user interface data to a display device, receiving input regarding the mineral deposit, and identifying the position of the mineral deposit based at least in part on the input. Moreover, in some implementations, the analyzing the pre-procedure image to identify the position of the mineral deposit on the native leaflet can comprise performing one or more image processing techniques with the pre-procedure image to identify the position of the mineral deposit on the native leaflet.

In some embodiments, the present disclosure relates to a computing system comprising control circuitry and memory communicatively coupled to the control circuitry and storing executable instructions that, when executed by the control circuitry, cause the control circuitry to perform operations. The operations can comprise receiving data indicative of a position of a mineral formation on a native leaflet of a native valve within a cardiac vessel, generating graphical interface data representing an image of a prosthetic valve implanted at the native valve, receiving input regarding a position of a mineral representation in the image, and based at least in part on the input and the data, determining a position of the native leaflet within the cardiac vessel. In some embodiments, the image comprises at least one of a computed tomography image or an x-ray image of the cardiac vessel.

In some implementations, the native valve comprises the aortic valve and the cardiac vessel comprises the aorta. In some embodiments, the operations further comprise, based at least in part on the position of the native leaflet within the cardiac vessel, determining an amount of access to a coronary artery. Moreover, in some embodiments, the operations further comprise identifying a position of at least a portion of the prosthetic valve within the aorta. The determining the amount of access to the coronary artery can be based at least in part on the position of at least the portion of the prosthetic valve within the aorta.

In some implementations, the data is indicative of a position of the mineral formation relative to an end of the native leaflet and the determining the position of the native leaflet within the cardiac vessel is based at least in part on the position of the mineral formation relative to the end of the native leaflet. Further, in some implementations, the data indicates one or more characteristics of the mineral formation, and the operations further comprise, based at least in part on the data, performing one or more image processing techniques with the image to determine that the mineral representation in the image represents the mineral formation on the native leaflet.

In some embodiments, the present disclosure relates to a method comprising obtaining, by control circuitry, an image representing a prosthetic valve implanted at a native valve within a cardiac vessel and receiving, by the control circuitry, data indicative of a position of a mineral formation on a native leaflet before implantation of the prosthetic valve. The method can also comprise analyzing the image to identify a position of the mineral formation within the cardiac vessel and, based at least in part on the position of the mineral representation and the data, determining a position of the native leaflet within the cardiac vessel.

In some implementations, the method further comprises, based at least in part on the position of the native leaflet within the cardiac vessel, determining an amount of access to a fluid vessel associated with the cardiac vessel. In some embodiments, the method further comprises identifying a position of at least a portion of the prosthetic valve within the cardiac vessel. The determining the amount of access to the fluid vessel can be based at least in part on the position of at least the portion of the prosthetic valve within the cardiac vessel. Moreover, in some embodiments, the method further comprises identifying a position of coapt leaflets within the cardiac vessel, based at least in part on the position of the coapt leaflets, determining an end of the native leaflet, determining a distance between the end of the native leaflet and the mineral formation. The determining the amount of access to the fluid vessel can be based at least in part on the distance between the end of the native leaflet and the mineral formation.

In some implementations, the data is indicative of a position of the mineral formation relative to an end of the native leaflet. The determining the position of the native leaflet within the cardiac vessel can be based at least in part on the position of the mineral formation relative to the end of the native leaflet. Moreover, in some implementations, the analyzing the image to identify the position of the mineral formation within the cardiac vessel comprises performing one or more image processing techniques with the image to identify the position of the mineral formation within the cardiac vessel.

In some embodiments, the present disclosure relates to a method comprising analyzing a first image to determine a position of a mineral deposit on a native leaflet within a cardiac vessel and analyzing a second image to identify a position of the mineral deposit within the cardiac vessel. The first image can represent a native valve and the second image can represent a prosthetic valve. The method can also comprise, based at least in part on the position of the mineral deposit on the native leaflet and the position of the mineral deposit within the cardiac vessel, determining access to a coronary artery, and providing an indication indicating a coronary access condition. The indication can be based at least in part on the determined access to the coronary artery. In some implementations, the indication indicates a risk level associated with performing a procedure that includes accessing the coronary artery.

In some implementations, the indication indicates an amount of access to the coronary artery. In some embodiments, the method further comprises determining that the amount of access to the coronary artery is less than a threshold and, based at least in part on determining that the amount of access to the coronary artery is less than the threshold, refraining from performing a procedure that includes accessing the coronary artery. Moreover, in some embodiments, the method further comprises determining that the amount of access to the coronary artery is greater than a threshold and, based at least in part on determining that the amount of access to the coronary artery is greater than the threshold, performing a procedure that includes accessing the coronary artery.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
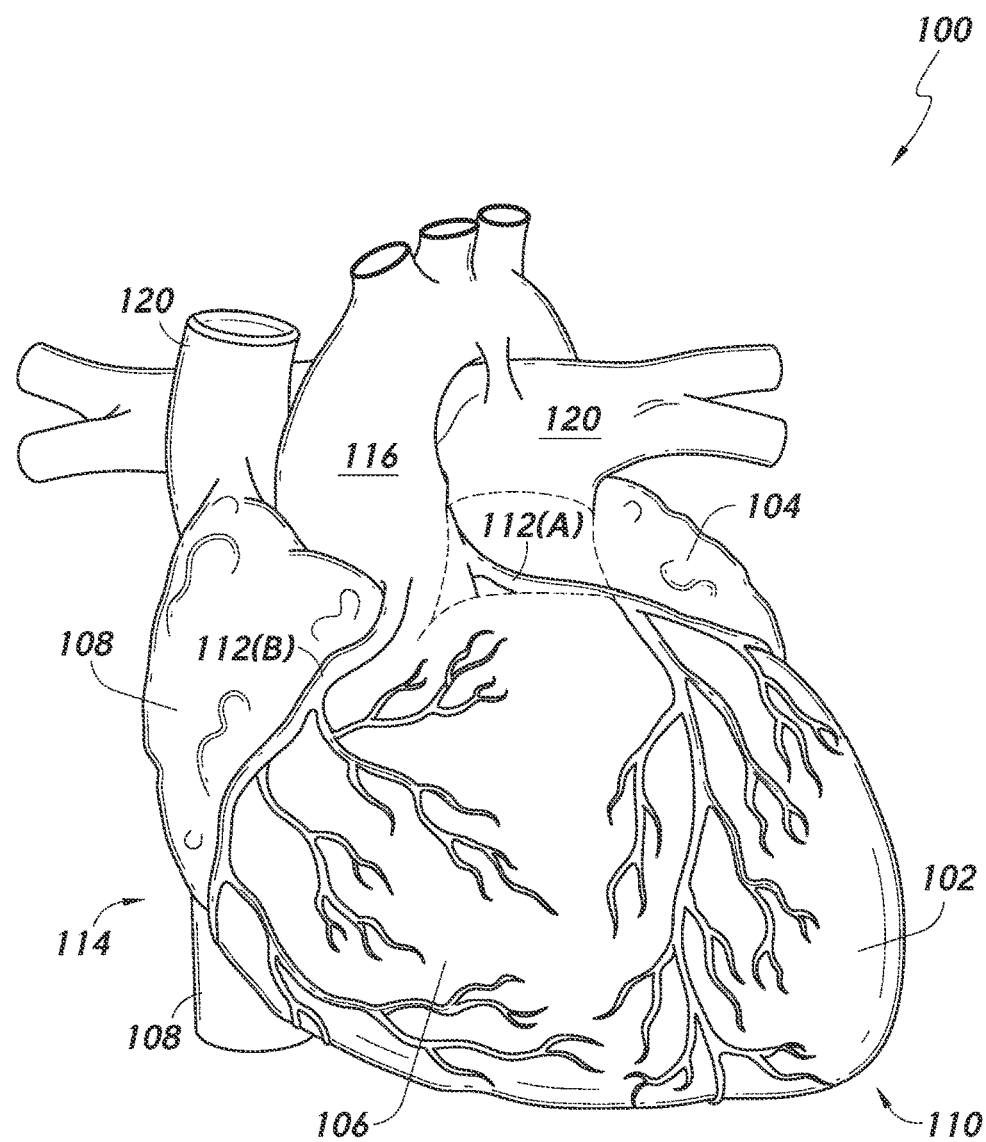
FIG. 1 illustrates a perspective view of an example heart in accordance with one or more embodiments.

The headings provided herein are for convenience only and do not necessarily affect the scope or meaning of the claimed subject matter. The present disclosure relates to systems, devices, and methods to determine access for an anatomical feature based on an analysis of one or more images representing a mineral deposit.

Although certain preferred embodiments and examples are disclosed below, the subject matter extends beyond the specifically disclosed embodiments to other alternative embodiments and/or uses, and to modifications and equivalents thereof. Thus, the scope of the claims that may arise here from is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Overview

As noted above, certain cases of aortic valve calcification or stenosis require the aortic valve to be replaced with a prosthetic valve. Prosthetic heart valve implantation can involve delivering a prosthetic valve to a native valve and deploying the prosthetic valve against the valve and/or surrounding anatomy. For example, when a prosthetic valve is implanted at the aortic valve, the native leaflets of the valve are displaced toward the aortic wall and surrounding anatomy. In some cases, one or more of the native leaflets can completely or partially block the coronary ostia, blocking access to the coronary arteries. To perform other procedures on the heart or surrounding anatomy in the future (sometimes referred to as "re-access procedures"), access may be required to the coronary arteries. For instance, in some re-access procedures, a physician can navigate a device, such as a scope or catheter, to the aortic valve through the aorta and attempt to travel into the coronary artery through the coronary ostium. However, the physician may be unaware that a native leaflet has been displaced to such a degree by a prosthetic valve that the native leaflet is blocking access to the coronary artery. Such blockage can result in unsuccessful re-access procedures and/or failure to perform a re-access procedure due to the likelihood of success.

This disclosure describes techniques and systems for determining access for an anatomical feature based on an analysis of one or more images representing a mineral deposit. In some embodiments, the techniques can estimate a position of a native valve after a prosthetic valve has been implanted therein. For example, the techniques can analyze a pre-procedure image of the native valve to determine a position of a mineral deposit on a native leaflet, such as a calcium deposit on the native leaflet. Following implantation of a prosthetic valve, the techniques can analyze a post-procedure image of the prosthetic valve to identify a position of the mineral deposit within the heart-valve area. Based on the position of the mineral deposit on the native leaflet (as determined from the pre-procedure image) and the position of the mineral deposit within the heart-valve area (as identified from the post-procedure image), the techniques can estimate a position of the native leaflet after the prosthetic valve implantation. Such information can be used to determine an amount of access (e.g., available space) to a vessel located within proximity to the native valve, such as the coronary arteries.

In many embodiments, the techniques and systems are discussed in the context of calcium and/or phosphate formations on a valve, such as in the case of aortic calcification/stenosis. However, the techniques and systems can be applied to a variety of contexts, such as other minerals and/or anatomical features.

Example Heart Anatomy

Figure 2:
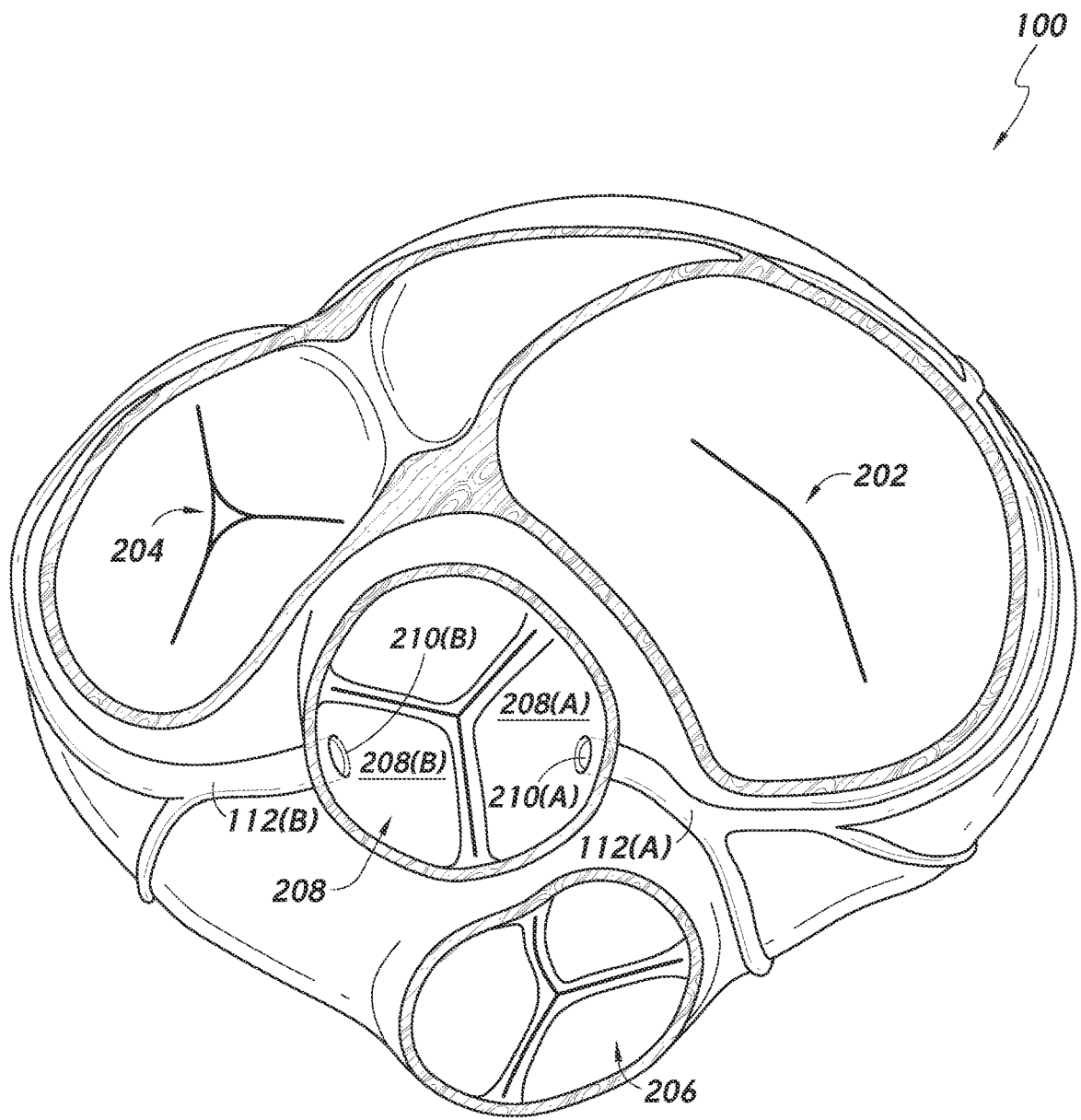
FIG. 2 illustrates a cross-sectional top view of an example heart in accordance with one or more embodiments.

FIGS. 1 and 2 illustrate an example heart 100 having various features relevant to certain aspects of the present disclosure. In particular, FIG. 1 illustrates a perspective view of the heart 100, while FIG. 2 illustrates a cross-sectional top view of the heart 100. The heart 100 includes four chambers, namely the left ventricle 102, the left atrium 104, the right ventricle 106, and the right atrium 108. A wall of muscle, referred to as the septum, separates the left-side chambers from the right-side chambers. In particular, an atrial septum wall portion separates the left atrium 104 from the right atrium 108, whereas a ventricular septum wall portion separates the left ventricle 102 from the right ventricle 106. The inferior tip 110 of the heart 100 is referred to as the apex and is generally located on or near the midclavicular line, in the fifth intercostal space.

The heart 100 includes four valves for aiding the circulation of blood therein. Heart valves can generally comprise a relatively dense fibrous ring, referred to herein as the annulus, as well as a plurality of leaflets or cusps attached to the annulus. Generally, the size and position of the leaflets or cusps can be such that when the heart contracts, the resulting increased blood pressure produced within the corresponding heart chamber forces the leaflets at least partially open to allow flow from the heart chamber. As the pressure in the heart chamber subsides, the pressure in the subsequent chamber or blood vessel can become dominant and press back against the leaflets. As a result, the leaflets/cusps come in apposition to each other, thereby closing the flow passage.

Surrounding the ventricles (102, 106) are a number of arteries 112 (sometimes referred to as "the coronary arteries 112") that supply oxygenated blood to the heart muscle and a number of veins (not shown) that return the blood from the heart muscle to the right atrium 108 via the coronary sinus, which is a relatively large vein that extends generally around the upper portion of the left ventricle 102 and provides a return conduit for blood returning to the right atrium 108.

The left ventricle 102 is the primary pumping chamber of the heart 100. A healthy left ventricle is generally conical or apical in shape in that it is longer (with respect to the mean electrical axis of the heart 100) than it is wide (with respect to a transverse axis extending between opposing walls of the left ventricle 102 at their widest point) and descends from a base 114 with a decreasing cross-sectional diameter and/or circumference to the point or apex 110. Generally, the apical region of the heart 100 can be considered the bottom region of the heart 100 that is within the left and/or right ventricular region but is distal to the mitral 202 and tricuspid 204 valves and disposed toward the tip 110 of the heart.

The pumping of blood from the left ventricle 102 is accomplished by a squeezing motion and a twisting or torsional motion. The squeezing motion occurs between the lateral walls of the left ventricle 102 and the septum. The twisting motion is a result of contraction of heart muscle fibers that extend in a generally circular or spiral direction around the heart 100. When these fibers contract, they produce a gradient of angular displacements of the myocardium from the apex 110 to the base 114 about the mean electrical axis of the heart 100. The resultant force vectors extend at angles from about 30-60 degrees to the flow of blood through the aortic valve 208 and ascending aorta 116. The contraction of the heart 100 is manifested as a counterclockwise rotation of the apex 110 relative to the base 114, when viewed from the apex 110 (i.e., inferior view of the heart 100). The contractions of the heart 100, in connection with the filling volumes of the left atrium 104 and ventricle 102, respectively, can result in relatively high fluid pressures in the left side of the heart 100 at least during certain phase(s) of the cardiac cycle.

The primary roles of the chambers of the left side of the heart 100 (i.e., left atrium 104 and left ventricle 102) are to act as holding chambers for blood returning from the lungs (not shown) and to act as a pump to transport blood to other areas of the heart 100. The left atrium 104 receives oxygenated blood from the lungs via the pulmonary veins. The oxygenated blood that is collected from the pulmonary veins in the left atrium 104 enters the left ventricle 102 through the mitral valve 202. In some patients, the walls of the left atrium 104 are slightly thicker than the walls of the right atrium 108. Deoxygenated blood enters the right atrium 108 through the inferior 118 and superior 120 venae cavae. The right side (i.e., right atrium 108 and right ventricle 106) of the heart 100 then pumps this deoxygenated blood into the pulmonary arteries 120 around the lungs. There, fresh oxygen enters the blood stream, and the blood moves to the left side of the heart 100 via the network of pulmonary veins that ultimately terminate at the left atrium 104. In FIG. 1, a portion of the pulmonary trunk is removed (i.e., shown with dotted lines) to expose the left coronary artery 112(A).

The valves of the heart 100 include the tricuspid valve 204, which separates the right atrium 108 from the right ventricle 106. The tricuspid valve 204 can generally have three cusps or leaflets and can generally close during ventricular contraction (i.e., systole) and open during ventricular expansion (i.e., diastole). The valves of the heart 100 further include the pulmonary valve 206, which separates the right ventricle 106 from the pulmonary artery 120 and can be configured to open during systole so that blood can be pumped toward the lungs, and close during diastole to prevent blood from leaking back into the heart 100 from the pulmonary artery 120. The pulmonary valve 206 generally has three cusps/leaflets, wherein each one can have a crescent-type shape. The heart 100 also includes the mitral valve 202, which generally has two cusps/leaflets and separates the left atrium 104 from the left ventricle 102. The mitral valve 202 can generally be configured to open during diastole so that blood in the left atrium 104 can flow into the left ventricle 102, and close during systole to prevent blood from leaking back into the left atrium 104. Further, the heart 100 includes the aortic valve 208, which separates the left ventricle 102 from the aorta 116. The aortic valve 208 generally has three cusps/leaflets, wherein each one can have a crescent-type shape. The aortic valve 208 is configured to open during systole to allow blood leaving the left ventricle 102 to enter the aorta 116, and close during diastole to prevent blood from leaking back into the left ventricle 102.

The atrioventricular (i.e., mitral and tricuspid) heart valves are generally associated with a sub-valvular apparatus, including a collection of chordae tendineae and papillary muscles securing the leaflets of the respective valves to promote and/or facilitate proper coaptation of the valve leaflets and prevent prolapse thereof. The papillary muscles, for example, can generally comprise finger-like projections from the ventricle walls. The chordae tendineae generally keep the valve leaflets from opening in the wrong direction, thereby preventing blood to flow back to the left atrium 104.

With further reference to the aortic anatomy of the heart 100, the ascending aorta generally begins at the opening of the aortic valve 208 in the left ventricle 102 of the heart. The ascending aorta can run through a common pericardial sheath with the pulmonary trunk. At the root of the ascending aorta, the blood vessel lumen may generally present three relatively small pockets (i.e., aortic sinuses or "sinuses of Valsalva") between the cusps of the aortic valve 208 and the wall of the aorta 116. The left aortic sinus contains the origin of the left coronary artery 112(A) (also referred to as "the LCA 112(A)") and the right aortic sinus likewise gives rise to the right coronary artery 112(B) (also referred to as "the RCA 112(B)"). The posterior aortic sinus does not give rise to a coronary artery.

FIG. 2 shows various features relevant to the coronary arteries 112. As noted above, the left coronary artery 112(A) and the right coronary artery 112(B) originate at the aortic sinus. The left coronary artery 112(A) originates above the left cusp 208(A) (also referred to as "the left leaflet 208(A)") of the aortic valve 208 and the right coronary artery 112(B) originates above the right cusp 208(B) (also referred to as "the right leaflet 208(B)") of the aortic valve 208. The root of the aorta 116 includes the coronary ostia 210 that connects to the coronary arteries 112, with the left coronary ostia 210(A) positioned above the left cusp 208(A) and the right coronary ostia 210(B) positioned above the right cusp 208(B).

Example Aortic Valve Calcification and Prosthetic Valve

Figure 3:
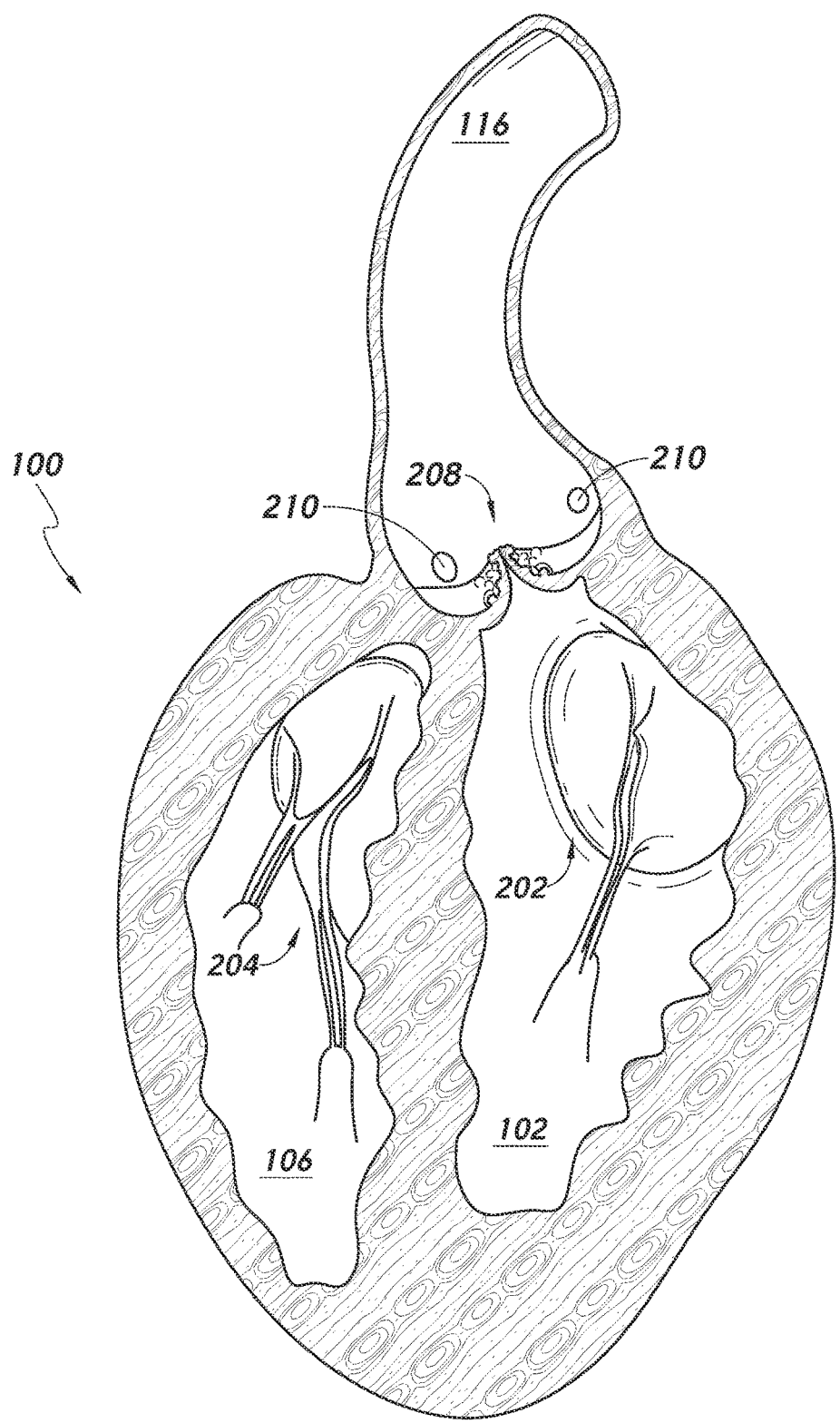
FIG. 3 illustrates a cross-sectional view of an example heart with mineral formations on the aortic valve in accordance with one or more embodiments.
Figure 4:
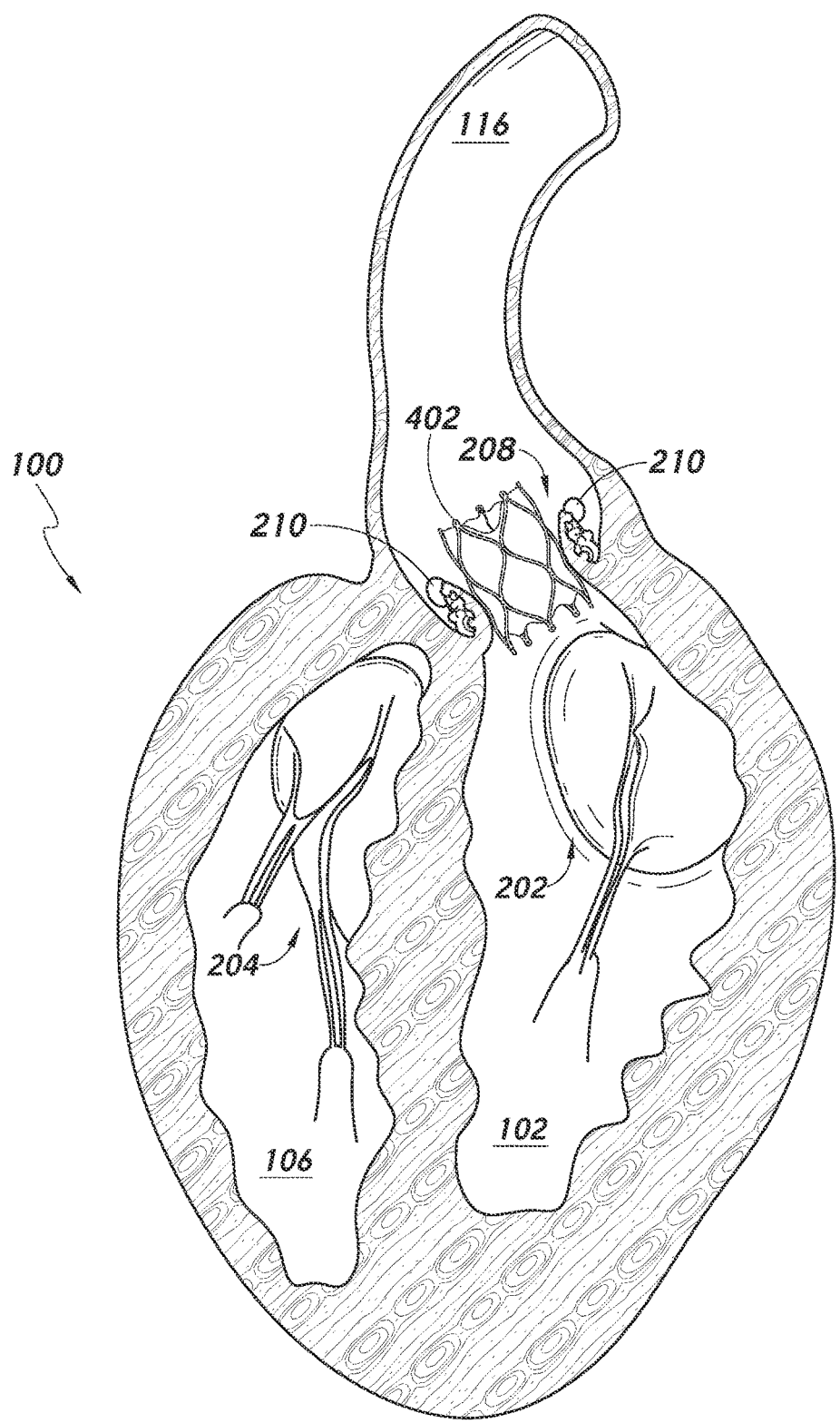
FIG. 4 illustrates an example cross-sectional view of the heart of FIG. 3 with a prosthetic valve implanted at the aortic valve in accordance with one or more embodiments.

FIGS. 3 and 4 illustrate cross-sectional views of the heart 100 with mineral formations on the aortic valve 208 in accordance with one or more embodiments. As used herein, the term "mineral formation" or "mineral deposit" can generally refer to one or more minerals embedded in and/or attached to an anatomical feature. For example, in FIGS. 3 and 4, calcium and/or phosphate is embedded in and/or attached to the aortic valve 208, such as on/or within the leaflets of the aortic valve 208. Although many example embodiments are discussed in the context of calcium and/or phosphate formations on the aortic valve, other types of mineral formations can occur on the aortic valve and/or other valves/anatomical features.

In the examples of FIGS. 3 and 4, the aortic valve 208 includes relatively severe calcification (e.g., aortic valve stenosis), requiring the replacement of the aortic valve 208 with a prosthetic valve 402 (shown in FIG. 4). In some embodiments, the prosthetic valve 402 can be implanted at the aortic valve 208 by performing a minimally invasive procedure. For example, a physician can make a relatively small incision (e.g., less than a threshold size) on a patient, such as on the patient's leg or chest, to access an anatomical lumen of the patient, such as an artery or vein. The physician can advance a catheter-based device into the anatomical lumen (e.g., the femoral vein/artery, the inferior vena cava, etc.) and navigate the catheter-based device to an implantation site, namely the aortic valve 208. Using the catheter-based device or another device (e.g., a balloon catheter), the physician can deploy the prosthetic valve 402 at the aortic valve 208 to replace the native aortic valve 208. In some embodiments, such procedure includes a transcatheter aortic valve replacement (TAVR) or transcatheter aortic valve implantation (TAVI) procedure that uses transcatheter access. Although some embodiments are discussed in the context of implanting a prosthetic valve using transcatheter access, a prosthetic valve can be implanted using other procedures, such as a more invasive procedure that includes cutting into the heart (e.g., to implant a surgical prosthetic valve).

In any event, when implanting the prosthetic valve 402, the leaflets of the aortic valve 208 can be displaced towards the aortic wall, as shown in FIG. 4. For example, the prosthetic valve 402 can expand radially and press the leaflets of the aortic valve 208 towards the aortic wall. In other words, a size/diameter of the prosthetic valve 402 can change to provide outward radial forces and displace the leaflets of the aortic valve 208 towards the aortic wall. Once implanted, the prosthetic valve 402 can continue to provide outward radial forces and maintain the leaflets of the aortic valve 208 in the position shown in FIG. 4. In some cases, with the native leaflets of the aortic valve 208 displaced towards the aortic wall, the native leaflets can limit access to the coronary arteries (not shown in FIGS. 3 and 4). That is, the native leaflets can obstruct access from the aorta 116 into the coronary arteries 112 via the coronary ostia 210.

The prosthetic valve 402 (sometimes referred to as "the artificial heart valve 402") can include a variety of types of prosthetic valves, such as catheter-based prosthetic valves (e.g., transcatheter heart valve (THV)), surgical prosthetic valves, and so on. In some embodiments, the prosthetic valve 402 is configured to be radially compressed into a compressed state for delivery through a patient's vasculature. The prosthetic valve 402 can be configured to self-expand to a natural, uncompressed or functional state having a preset diameter once positioned in a desirable location within the patient's vasculature.

In some embodiments, the prosthetic valve 402 can include a support frame, which can comprise a grated framework, such as a stent, configured to secure the prosthetic valve 402 within or adjacent to a defective valve annulus of the heart 100. The support stent structure can further provide stability and prevent the prosthetic valve 402 from migrating after it has been implanted. The support stent structure can comprise any suitable or desirable material, such as memory metal, metal alloys such as stainless steel or cobalt chromium, and/or polymers. Furthermore, the support stent structure can have configurations other than that shown in FIG. 4. For example, the support stent structure can have a different shape, more or fewer vertical support bars, and/or additional structures for added stability. In certain embodiments, the support stent structure can comprise a strut mesh and/or sleeve structure.

In some embodiments, the support stent structure can be secured to a valve leaflet assembly. The valve leaflet assembly can include a plurality of leaflets that collectively function as a one-way valve by coapting with one another. With respect to, for example, prosthetic aortic valves, a valve leaflet assembly can comprise three leaflets. However, it will be appreciated that prosthetic valves can have a greater or lesser number of leaflets. The various components of the valve leaflet assembly can be wholly or partly formed of any suitable biological material or polymer such as, for example, polyethylene terephthalate (PET), ultra-high-molecular-weight polyethylene (UHMWPE), polytetrafluoroethylene (PTFE), or the like.

Example Architecture

Figure 5:
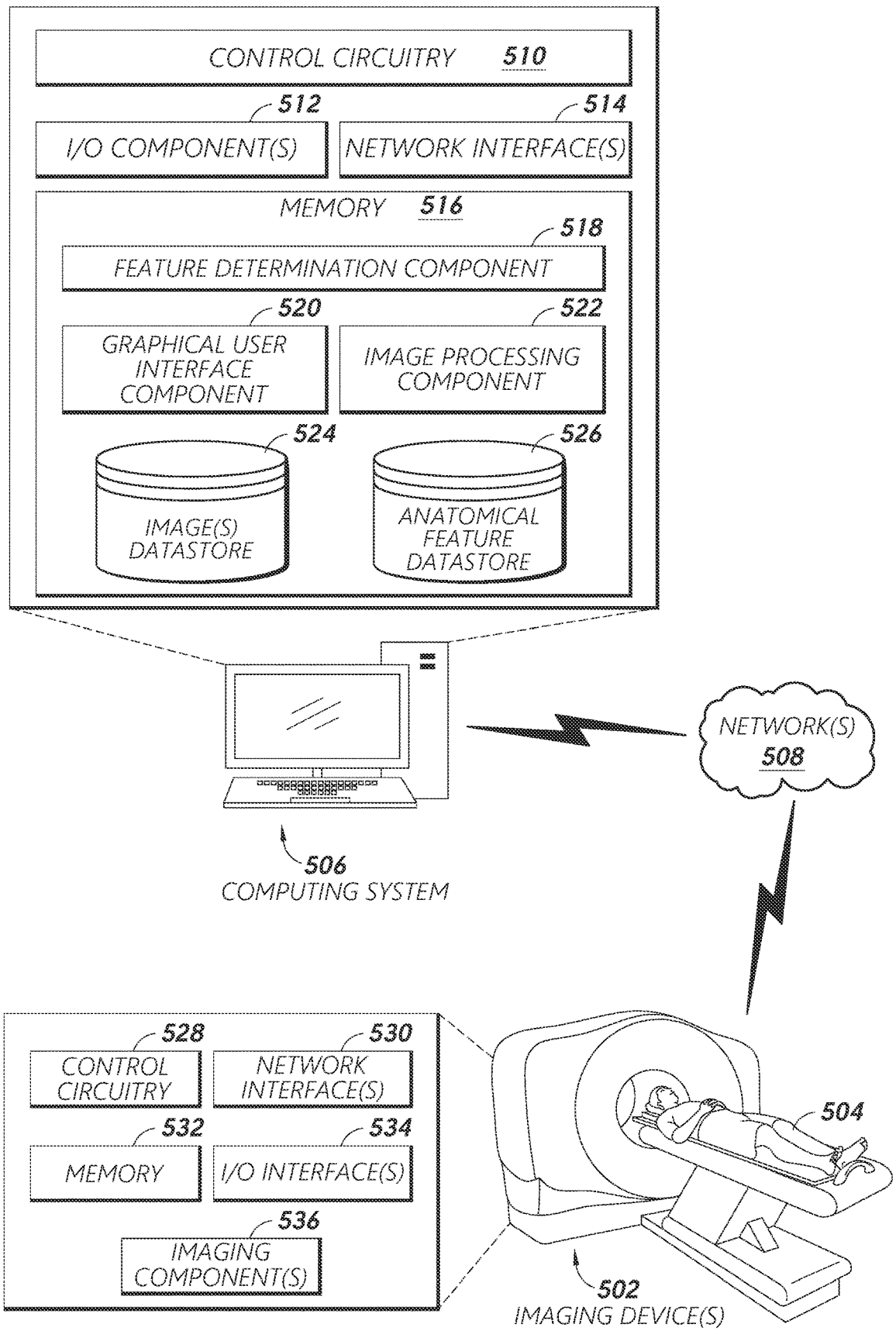
FIG. 5 illustrates an example architecture to determine access for an anatomical feature based on an analysis of one or more images representing a mineral deposit in accordance with one or more embodiments.

FIG. 5 illustrates an example architecture 500 to determine access for an anatomical feature based on an analysis of one or more images representing a mineral deposit in accordance with one or more embodiments. The architecture 500 includes one or more imaging devices 502 (referred to as "the imaging device 502," for ease of discussion) configured to capture/generate one or more images of a patient 504 and one or more computing systems 506 (referred to as "the computing system 506," for ease of discussion) configured to evaluate the one or more images to determine access for an anatomical feature associated with the patient 502. The imaging device 502 and the computing system 506 can be configured to communicate over one or more networks 508, such as to send/receive data including one or more images created by the imaging device 502 and/or any other data. The computing system 506 can be configured to receive input from and/or provide output to a user, such as a physician, a technician, a radiologist, and so on.

In some embodiments, the imaging device 502 can be configured to generate one or more pre-procedure images of the patient 504 before implantation of a prosthetic valve and provide the one or more pre-procedure images to the computing system 506. The computing system 506 can interface with a physician or operate independently to determine a position/characteristic of one or more mineral formations on a native valve based on the one or more pre-procedure images. Following or during implantation of the prosthetic valve, the imaging device 502 can be configured to generate one or more procedure or post-procedure images of the patient 504 and provide the one or more procedure or post-procedure images to the computing system 506. The computing system 506 can interface with a physician or operate independently to identify a position of the one or more mineral formations within the cardiac vessel. Further, the computing system 506 can use pre-procedure data indicative of the position of the one or more mineral formations to determine a position of a native valve within the cardiac vessel, which may generally be a displacement position that is due to the implantation of the prosthetic valve. Moreover, the computing system 506 can determine a position of the prosthetic valve within the cardiac vessel. Based on the position of the native valve and/or the prosthetic valve, the computing system 506 can determine an amount of space available to access a fluid vessel within the cardiac vessel, such as the coronary artery.

Although the computing system 506 and the imaging device 502 are discussed in many embodiments as performing both pre-procedure and post-procedure processing, the computing system 506 and/or the imaging device 502 can be implemented as one or more devices/systems, which can perform pre-procedure and/or post-procedure processing. In some embodiments, a first computing system and/or imaging device can be used to perform pre-procedure processing, while a second computing system and/or imaging device can be used to perform post-procedure processing. Further, in some embodiments, the imaging device 502 and the computing system 506 are located at the same facility/environment/location, while in other embodiments the imaging device and the computing system 506 are located at separate facilities/environments/locations.

The computing system 506 can be implemented as one or more computing devices, such as one or more desktop computers, laptops computers, servers, smartphones, electronic reader devices, mobile handsets, personal digital assistants, portable navigation devices, portable gaming devices, tablet computers, wearable devices (e.g., a watch, optical head-mounted display, etc.), portable media players, televisions, set-top boxes, computer systems in a vehicle, appliances, cameras, security systems, home-based computer systems, projectors, medical monitors, and so on. In some embodiments, the one or more computing devices are configured in a cluster, data center, cloud computing environment, or a combination thereof. Further, in some embodiments, the one or more computing devices are implemented as a remote computing resource that is located remotely to the imaging device 502. In other embodiments, the one or more computing devices are implemented as local resources that are located locally at an environment of the imaging device 502.

As illustrated, the computing system 506 can include one or more of the following components, devices, modules, and/or units (referred to herein as "components"), either separately/individually and/or in combination/collectively: control circuitry 510, one or more I/O components 512, one or more network interfaces 514, and/or data storage/memory 516. Although certain components of the computing system 506 are illustrated in FIG. 5, it should be understood that additional components not shown can be included in embodiments in accordance with the present disclosure. Furthermore, certain of the illustrated components can be omitted in some embodiments. Although the control circuitry 510 is illustrated as a separate component in the diagram of FIG. 5, it should be understood that any or all of the remaining components of the computing system 506 can be embodied at least in part in the control circuitry 510. That is, the control circuitry 510 can include various devices (active and/or passive), semiconductor materials and/or areas, layers, regions, and/or portions thereof, conductors, leads, vias, connections, and/or the like, wherein one or more of the other components of the computing system 506 and/or portion(s) thereof can be formed and/or embodied at least in part in/by such circuitry components/devices.

The various components of the computing system 506 can be electrically and/or communicatively coupled using certain connectivity circuitry/devices/features, which may or may not be part of the control circuitry 510. For example, the connectivity feature(s) can include one or more printed circuit boards configured to facilitate mounting and/or interconnectivity of at least some of the various components/circuitry of the computing system 506. In some embodiments, two or more of the control circuitry 510, the one or more I/O components 512, the one or more network interfaces 514, and/or the data storage/memory 516, can be electrically and/or communicatively coupled to each other.

The one or more I/O components 512 can include a variety of components to receive input and/or provide output, such as to interface with a user. The one or more I/O components 512 can be configured to receive touch, speech, gesture, or any other type of input. Further, the one or more I/O components 512 can be configured to output display data, audio data, haptic feedback data, or any other type of output data. The one or more I/O components 512 can include the one or more displays (sometimes referred to as "one or more display devices"), touchscreens, touch pads, controllers, mice, keyboards, wearable devices (e.g., optical head-mounted display), virtual or augmented reality devices (e.g., head-mounted display), speakers (e.g., configured to output sounds based on audio signals), microphones (e.g., configured to receive sounds and generate audio signals), cameras, and so on. The one or more displays can include one or more liquid-crystal displays (LCD), light-emitting diode (LED) displays, organic LED displays, plasma displays, electronic paper displays, and/or any other type(s) of technology. In some embodiments, the one or more displays include one or more touchscreens configured to receive input and/or display data.

The one or more network interfaces 514 can be configured to communicate with one or more devices/systems over the one or more networks 508. For example, the one or more network interfaces 514 can send/receive data in a wireless and/or wired manner over a network, such as one or more images captured by the imaging device 502. The one or more networks 508 can include one or more local area networks (LAN), wide area networks (WAN) (e.g., the Internet), personal area networks (PAN), body area networks (BAN), etc. In some embodiments, the one or more network interfaces 514 can implement a wireless technology such as Bluetooth, Wi-Fi, near field communication (NFC), or the like.

As illustrated, the memory 516 can include a feature determination component 518, a graphical user interface component 520, and/or image processing component 522 configured to facilitate various functionality discussed herein. In some embodiments, one or more of the components 518-522 can include and/or be implemented as one or more executable instructions that, when executed by the control circuitry 510, cause the control circuitry 510 to perform one or more operations. Although many embodiments are discussed in the context of the components 518-522 including one or more instructions that are executable by the control circuitry 512, any of the components 518-522 can be implemented at least in part as one or more hardware logic components, such as one or more application specific integrated circuits (ASIC), one or more field-programmable gate arrays (FPGAs), one or more program-specific standard products (ASSPs), one or more complex programmable logic devices (CPLDs), and/or the like. Furthermore, although the components 518-522 are illustrated as being included within the computing system 506, any of the components 518-522 can be implemented at least in part within another device/system, such as the imaging device 502 and/or another device/system. Similarly, any of the other components of the computing system 506 can be implemented at least in part within another device/system.

The feature determination component 518 can be configured to identify one or more anatomical features and/or characteristics/positions of the one or more anatomical features. For example, the feature determination component 518 can evaluate one or more pre-procedure images captured by the imaging device 502 and/or stored in an image datastore 524. The one or more pre-procedure images can represent one or more features of the patient 504 before a medical device is implanted into the patient 504, such as before a prosthetic valve is implanted within a cardiac vessel. The evaluation of the one or more pre-procedure images can determine one or more characteristics/positions of one or more anatomical features within the patient 504. For example, the feature determination component 518 can determine a characteristic/position of a native leaflet (e.g., a position of the native leaflet within a cardiac vessel, a length of the leaflet, a distance from an end of a leaflet to a particular plane, a position of an end of a native leaflet based on coapt leaflets, etc.), a characteristic/position of a mineral deposit (e.g., a position of the mineral deposit on the native leaflet, dimensions of the mineral deposit, etc.), a characteristic/position of surrounding anatomy of the native leaflet (e.g., a diameter of a coronary artery, a diameter of the aorta, a distance from an annulus plane and a bottom plane of the coronary artery ostium, etc.), a characteristic/position of coapt leaflets (e.g., a position of coapt leaflets), and so on. The feature determination component 518 can store data indicative of such characteristics/positions in an anatomical feature datastore 526 (sometimes referred to as "pre-procedure data").

Further, the feature determination component 518 can evaluate one or more procedure or post-procedure images captured by the imaging device 502 and/or stored in an image datastore 524. The one or more procedure or post-procedure images can represent one or more features of the patient 504 while a medical device is being implanted into the patient 504 and/or after a medical device has been implanted, such as after a prosthetic valve is implanted within a cardiac vessel. The evaluation of the one or more procedure or post-procedure images can determine one or more characteristic/positions of one or more anatomical features within the patient 504 during/after the procedure. For example, the feature determination component 518 can determine one or more characteristics/positions relating to the aortic annular/valve region, such as a characteristic/position of a native leaflet during/after a procedure, a characteristic/position of a mineral deposit on a native leaflet during/after a procedure, a characteristic/position of surrounding anatomy of the native leaflet during/after a procedure, an amount of access to an anatomical feature during/after a procedure (e.g., an amount of access to the coronary artery), and so on. The feature determination component 518 can store data indicative of such characteristics/positions in the anatomical feature datastore 526 (sometimes referred to as "procedure data" or "post-procedure data").

In evaluating one or more procedure or post-procedure images, the feature determination component 518 can reference data stored in the anatomical feature datastore 526, such as pre-procedure data. For example, the feature determination component 518 can identify a calcium representation in a post-procedure image and determine that the calcium representation corresponds to a particular calcium deposit on a native leaflet based on pre-procedure data indicating a characteristic of the particular calcium deposit (e.g., dimensions of the calcium deposit). Further, the feature determination component 518 can also determine a position of the native leaflet within the cardiac vessel based on the pre-procedure data, which can indicate a position of the calcium deposit on the native leaflet, such as a distance from the end of the native leaflet to the calcium deposit. Moreover, the feature determination component 518 can determine an amount of access to a fluid vessel located within proximity to the native leaflet (e.g., determine how much the position of the native leaflet blocks access to the fluid vessel). For example, it can be determined if there is sufficient space around a native leaflet (which may now partially cover the coronary ostia) for a medical instrument to access the coronary artery from the aorta.

In some embodiments, the feature determination component 518 can evaluate one or more pre-procedure, procedure, and/or post-procedure images to identify anatomical features that are visible/represented in the one or more images, such as walls, calcium deposits, coapt leaflets, cavities, and/or other anatomical features that are visible/represented. Based on identifying such visible/represented anatomical features, the feature determination component 518 can determine characteristics/positions for the visible/represented anatomical features. Further, the feature determination component 518 can identify hidden/non-represented anatomical features and/or characteristics/positions of the hidden/non-represented anatomical features based on the characteristics/positions of the visible/represented anatomical features. The feature determination component 518 can store characteristics/positions regarding represented and/or non-represented anatomical features in the anatomical feature datastore 526.

In some embodiments, the feature determination component 518 can evaluate multiple pre-procedure, procedure, and/or post-procedure from different orientations/positions/angles. For example, the feature determination component 518 can identify one or more characteristics/positions of an anatomical feature by analyzing a first image from a first orientation/position within a patient and analyzing a second image from a second orientation/position within the patient.

Example characteristics/positions of one or more anatomical features can include: a characteristic/position of a native leaflet (e.g., a thickness/length/width/shape of the native leaflet, a position of the native leaflet within a cardiac vessel, a distance from an end of the native leaflet to a particular plane, a position of an end of the native leaflet based on coapt leaflets, etc.), a characteristic/position of a mineral formation (e.g., a thickness/length/width/shape of the mineral formation, a position of the mineral formation on a native leaflet, a position of the mineral formation within a cardiac vessel, etc.), a characteristic/position of a fluid vessel (e.g., a diameter of the coronary artery, a diameter of the aorta/aortic root, etc.), a characteristic/position of an opening (e.g., a position of the coronary ostium within the aortic annuls region and/or relative to a native leaflet/prosthetic valve, etc.), and/or any other characteristics/dimension. In some embodiments, a position of an anatomical feature is represented/indicated with a dimension, such as a distance to another anatomical feature, a distance to a prosthetic valve, a distance to a mineral formation, etc. Further, in some embodiments, a position of an anatomical feature can include one or more coordinates of the anatomical feature within a coordinate system/space.

In some embodiments, one or more characteristics/positions of an anatomical feature can include one or more characteristics/positions of devices implanted at the anatomical feature, such as a size/shape/position of a prosthetic valve implanted within the human anatomy. Further, in some embodiments, one or more characteristics/positions of an anatomical feature can include one or more characteristics/positions of a mineral formation attached to and/or embedded in the anatomical feature. Moreover, in some embodiments, one or more characteristics/positions of an anatomical feature can include a characteristic/position of a visual representation of the anatomical feature in an image, such as a size of the visual representation, a color/shading of the visual representation, a position of the visual representation within the image, and so on.

In some embodiments, the feature determination component 518 operates in cooperation with the graphical user interface component 520. For example, the graphical user interface component 520 can be configured to provide an interface that includes an image. A user, such as a physician or technician, can view the image and provide input regarding a characteristic of an anatomical feature. In one example, the user can designate a representation in an image as representing a particular anatomical feature, such as a calcium deposit, leaflet, coronary artery, aortic wall, etc. In another example, a user can designate a first point/location on an image and a second point/location in the image and provide input requesting that a distance be calculated between the first point/location and the second point/location. The user can also provide input to label the distance. In examples, a user can provide input to determine/label any of the example dimensions discussed in FIGS. 6 and 7. In examples, the feature determination component 518 can use input provided by a user to evaluate one or more images and/or store data regarding one or more characteristics/positions of one or more anatomical features in the anatomical feature datastore in 526.

Further, in some embodiments, the feature determination component 518 operates in cooperation with the image processing component 522 to evaluate an image. For example, the image processing component 522 can perform one or more image processing techniques with one or more images to automatically identify image-based features within the one or more images and/or classify the one or more image-based features as anatomical features. In some embodiments, the image processing component 522 uses one or more artificial intelligence techniques, such as one or more machine-trained models, to analyze one or more images. In examples, the feature determination component 518 can use information determined by the image processing component 522 to evaluate one or more images and/or store data regarding characteristics/positions of one or more anatomical features in the anatomical feature datastore in 526.

In some embodiments, one or more of the components 518-522 evaluate one or more images to identify anatomical features that may not generally be visible/represented in the one or more images. For example, a native leaflet may not be visible/represented in an image of a cardiac vessel due to the characteristics of the native leaflet (e.g., the size/dimensions of the native leaflet), characteristics of the imaging device 502 (e.g., a detectable resolution of the imaging device 502), etc. To illustrate, the imaging device 502 can be configured to detect anatomical features that are larger than a particular size/thickness and a native leaflet may be smaller than that particular size/thickness. In some embodiments, a native leaflet may not be detected due to a proximity of the native leaflet to a prosthetic valve, which can have a larger size than the native leaflet and/or other characteristics that result in the imaging device 502 detecting a stronger signal from the prosthetic valve. That is, a signal from a prosthetic valve can be stronger than a signal from a native leaflet, causing the native leaflet to be undetected.

In some embodiments, although a single leaflet may not be visible/represented in an image, coapt leaflets may be visible/represented in an image. A position/characteristic of the coapt leaflets can be used to determine a tip/end of a native leaflet. For example, one or more of the components 518-522 can evaluate an image to identify coapt leaflets and determine characteristics/positions of the coapt leaflets and/or other anatomical features within the cardiac vessel, such as a distance from a mineral deposit to a tip of a native leaflet (i.e., the coapt leaflets).

Data/information generated/determined herein can be used in a variety of manners. In some embodiments, data regarding a characteristic/position of an anatomical feature can be used to determine whether a procedure can be performed, such as a re-access procedure. For example, the computing system 506 can generate data indicative of an amount of access to the coronary artery after implantation of a prosthetic valve at the aortic valve. Such data can be used to determine if a medical instrument, such as a catheter, can access the coronary artery from the aorta. In examples, if the amount of available space is two to three times larger than a diameter of a medical instrument, it can be determined that there is sufficient space for accessing the coronary artery with the medical instrument. In examples, access to the coronary artery can occur above/around/through a prosthetic valve, such as through a frame of the prosthetic valve, and/or above/around a native leaflet. In examples, data regarding an amount of access to an anatomical feature, such as the coronary artery, can be provided to a user, such as a physician, a technician, a patient, and so on, to assist the user in making decisions regarding the likelihood of success in performing a procedure after the implantation of a prosthetic valve and/or in selecting patients that are suited for a procedure. In examples, such information can be displayed to a user via a user interface.

Moreover, in some embodiments, data regarding a characteristic/position of an anatomical feature can be used to generate instructions/information to perform a procedure, such as information indicating where/how a medical instrument should access the coronary artery from the aorta. The procedure can be performed by a physician and/or a robotic system (e.g., a robotically controlled procedure). Further, in some embodiments, data regarding a characteristic/position of an anatomical feature can be used during a procedure, such as to initially implant a prosthetic valve, and/or after a procedure to reposition the prosthetic valve. Such data can assist in positioning or repositioning the prosthetic valve with the appropriate location to minimize blockage to the coronary artery and/or other anatomical features. Additionally, in some embodiments, data regarding a characteristic/position of an anatomical feature can be used to implant an additional prosthetic valve within an implanted prosthetic valve (sometimes referred to as a "TAVI-in-TAVI procedure"). Further, in some embodiments, data regarding a characteristic/position of an anatomical feature can be collected from multiple patients and used to determine metrics regarding the multiple patients, such as average positions of native leaflets, average amounts of available space to access a fluid vessel, and so on. In examples, such metrics can be provided to a user to assist in making decisions regarding performance of a procedure.

As noted above, the image datastore 524 can store one or more images, such as pre-procedure images, procedure images, and/or post-procedure images. The image datastore 524 can store images from the imaging device 502 and/or other imaging devices. Similarly, the anatomical feature datastore 526 can store data regarding characteristics/positions of pre-procedure anatomical features, procedure anatomical features, and/or post-procedure anatomical features. The anatomical feature datastore 526 can store data determined/generated by the feature determination component 518, the graphical user interface component 520, the image processing component 522, and/or another device/system. Although the image datastore 524 and the anatomical feature datastore 526 are illustrated as being included within the computing system 506, in some embodiments, the image datastore 524 and/or the anatomical feature datastore 526 can be implemented elsewhere, such as within a remote resource.

The imaging device 502 can be implemented as one or more computed tomography (CT) or computerized axial tomography (CAT) devices, magnetic resonance imaging (MRI) devices, x-ray devices, ultrasound devices, infrared thermography (IRT) devices, positron-emission tomography (PET) devices, and/or other types of medical imaging devices. The imaging device 502 can generally be configured to capture/generate one or more images including visual representations of interior anatomy, such as of the organs/tissues/other anatomical features of a patient. In some embodiments, the imaging device 502 captures/generates one or more images from different orientations/angles of the patient 504. This can allow the anatomy of the patient 504 to be viewed with different slices of data and/or from different orientations. The imaging device 502 can be configured to produce two-dimensional (2D) images, three-dimensional (3D) images, models, and so on. In some embodiments, a contrast dye or other substance is used to assist in capturing/generating an image. For example, the patient may be required to ingest a substance with contrast die to assist in capturing/generating an image with the imaging device 502.

As illustrated, imaging device 502 can include one or more of the following components, devices, modules, and/or units (referred to herein as "components"), either separately/individually and/or in combination/collectively: control circuitry 528, one or more network interfaces 530, data storage/memory 532, one or more I/O components 534, and one or more imaging components 536. Although certain components of the imaging device 502 are illustrated in FIG. 5, it should be understood that additional components not shown can be included in embodiments in accordance with the present disclosure. Furthermore, certain of the illustrated components can be omitted in some embodiments. Although the control circuitry 528 is illustrated as a separate component in the diagram of FIG. 5, it should be understood that any or all of the remaining components of the imaging device 502 can be embodied at least in part in the control circuitry 528. That is, the control circuitry 528 can include various devices (active and/or passive), semiconductor materials and/or areas, layers, regions, and/or portions thereof, conductors, leads, vias, connections, and/or the like, wherein one or more of the other components of the imaging device 502 and/or portion(s) thereof can be formed and/or embodied at least in part in/by such circuitry components/devices.

The various components of the imaging device 502 can be electrically and/or communicatively coupled using certain connectivity circuitry/devices/features, which may or may not be part of the control circuitry 528. For example, the connectivity feature(s) can include one or more printed circuit boards configured to facilitate mounting and/or interconnectivity of at least some of the various components/circuitry of the imaging device 502. In some embodiments, two or more of the control circuitry 528, the one or more network interfaces 530, the data storage/memory 532, the one or more I/O components 534, and/or the one or more imaging components 536, can be electrically and/or communicatively coupled to each other.

The one or more network interfaces 530 can be configured to communicate with one or more device/systems over the one or more networks 508. For example, the one or more network interfaces 530 can send/receive data in a wireless and/or wired manner over a network, such as one or more images. In some embodiments, the one or more network interfaces 530 can implement a wireless technology such as Bluetooth, Wi-Fi, near field communication (NFC), or the like.

The one or more I/O components 534 can include a variety of components to receive input and/or provide output, such as to interface with a user. The one or more I/O components 534 can be configured to receive touch, speech, gesture, or any other type of input. Further, the one or more I/O components 534 can be configured to output display data, audio data, haptic feedback data, or any other type of output data. The one or more I/O components 534 can include the one or more displays (sometimes referred to as "one or more display devices"), touchscreens, touch pads, controllers, mice, keyboards, wearable devices (e.g., optical head-mounted display), virtual or augmented reality devices (e.g., head-mounted display), speakers (e.g., configured to output sounds based on audio signals), microphones (e.g., configured to receive sounds and generate audio signals), cameras, and so on. The one or more displays can include one or more liquid-crystal displays (LCD), light-emitting diode (LED) displays, organic LED displays, plasma displays, electronic paper displays, and/or any other type(s) of technology. In some embodiments, the one or more displays include one or more touchscreens configured to receive input and/or display data.

The one or more imaging components 536 can include generators, sensors, detectors, cameras, etc. configured to provide/generate signals/radiation and/or to receive/detect signals/radiation, which can be used to capture/generate one or more images. In some embodiments, the imaging device 502 can include a structure to hold the patient 504 and/or move the patient 504 within proximity to the one or more imaging components 536.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Example Cardiac Vessels

Figure 6:
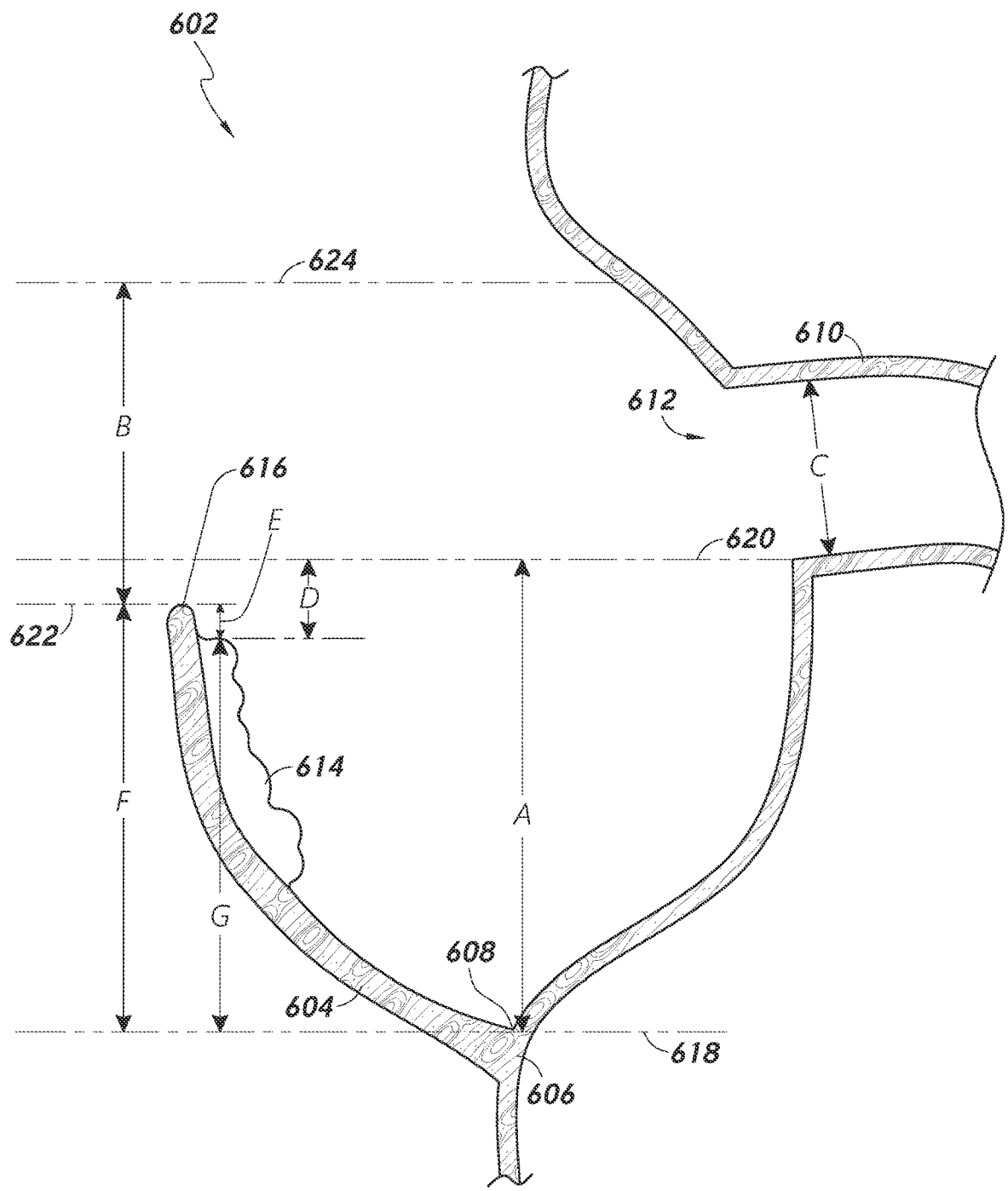
FIG. 6 illustrates a cross-sectional view of an example native leaflet and mineral formation in accordance with one or more embodiments.
Figure 7:
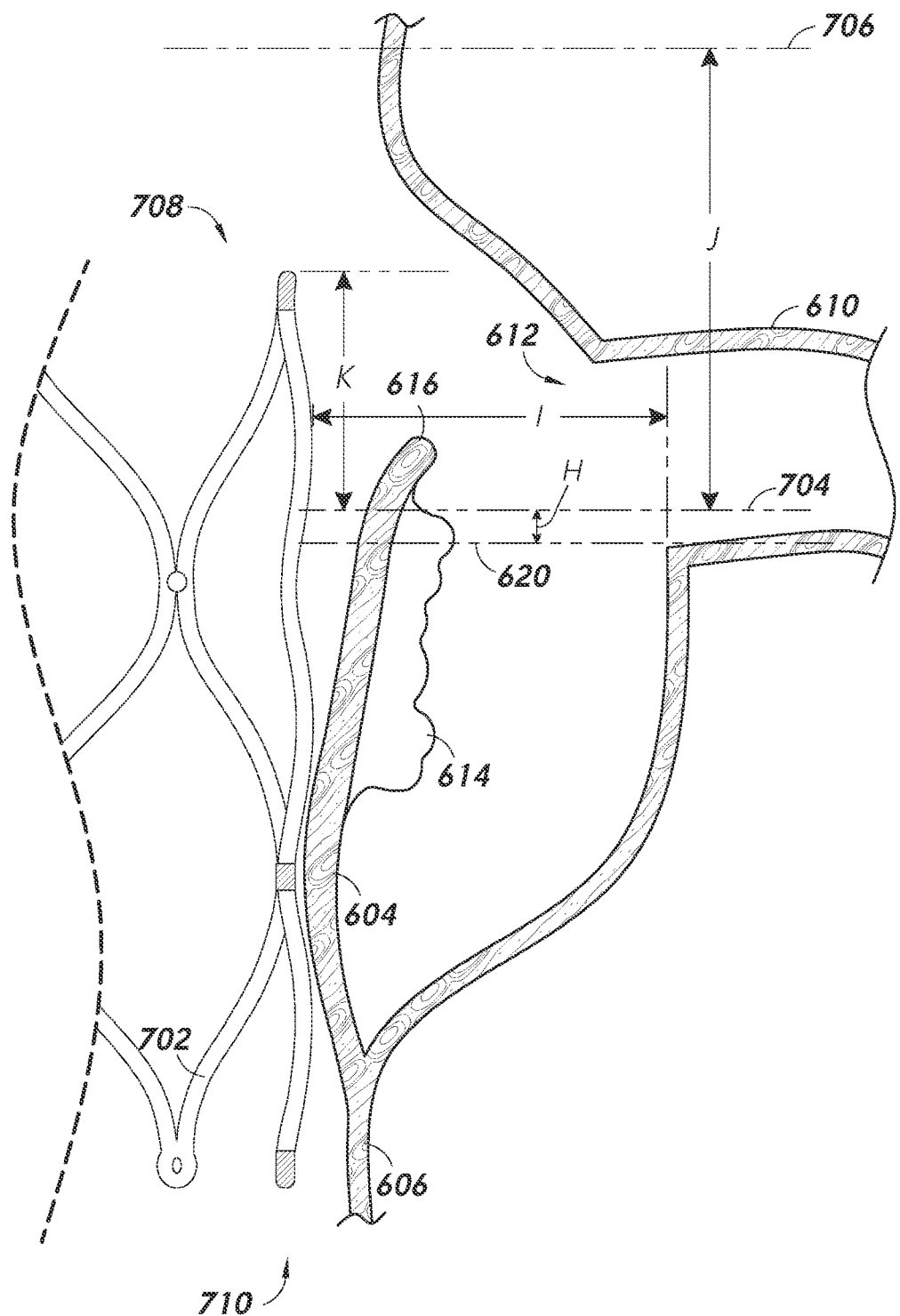
FIG. 7 illustrates a cross-sectional view of example native leaflet, mineral formation, and prosthetic valve in accordance with one or more embodiments.

FIGS. 6 and 7 illustrate cross-sectional views of example anatomical features and characteristics/positions of the anatomical features in accordance with one or more embodiments. In particular, FIGS. 6 and 7 illustrate anatomical features associated with the aorta 602, namely the aortic annular/valve region, including a native leaflet 604 attached to the aortic annulus 606 at an end 608 of the native leaflet 604 and the coronary artery 610 fluidly connected to the aorta 602 via the coronary ostium 612. As shown, the native leaflet 604 includes a calcium deposit 614 embedded and/or attached to the native leaflet 604. In these examples, the coronary artery 610 is the left coronary artery, which may have a higher risk for obstruction upon prosthetic valve implantation in comparison to the right coronary artery, in some cases. However, it should be appreciated that the description regarding the left coronary artery 610 can similarly be applicable to the right coronary artery (not shown), another type of fluid vessel, and/or any other anatomical feature. FIG. 6 illustrates the native leaflet 604 in a pre-procedure state without a prosthetic valve 702 implanted within the aortic valve, while FIG. 7 illustrates the native leaflet 604 in a post-procedure state with the prosthetic valve 702 implanted within the aortic valve.

In some embodiments, the techniques and systems discussed herein can evaluate one or more pre-procedure images representing the anatomical features shown in FIG. 6 to identify anatomical features that are visible/represented in the one or more pre-procedure images, such as an aortic wall(s), the calcium deposit 614, a leaflet tip/end (e.g., based on coapt leaflets), the coronary artery 610, and/or other anatomical features that are visible/represented. In some examples of evaluating the one or more pre-procedure images, a native leaflet tip/end can be identified when the leaflet is coapt with another leaflet, such as during a closed/diastolic phase. Based on identifying anatomical features that are visible/represented in the one or more pre-procedure images, the techniques and systems can determine characteristics/positions for the visible/represented anatomical features (and/or hidden/non-represented anatomical features), with the positioning being represented with one or more dimensions.

FIG. 6 shows some example dimensions (which can represent/identify positions of anatomical features) that can be determined for one or more pre-procedure images, including: a distance/dimension A between a plane 618 of the annulus and a plane 620 of the coronary artery ostium 612 (also referred to as "the lower plane 620"); a distance/dimension B between a plane 622 of the native leaflet coaptation and a native commissural plane 624; a diameter/dimension C the coronary artery 610 (which can represent the diameter of the left coronary artery 610 proximate to its ostium 612); a distance/dimension D between an upper end of the calcium deposit 614 and the bottom plane 620 of the coronary artery ostium 612; a distance/dimension E between an upper end 616 of the calcium deposit 614 and the end 616 of the leaflet 604; a distance/dimension F between the plane 618 of the annulus and the plane 622 of the native leaflets coaptation; and/or a distance/dimension G between the upper end of the calcium deposit 614 and the plane 618 of the annulus.

In some embodiments, if the upper end of the calcium deposit 614 is positioned below to the plane 620 of the coronary artery ostium 612 during diastole, as shown in FIG. 6, the distance D can be associated with an identifier to indicate such (e.g., a positive sign (+)). Further, if the upper end of the calcium deposit 614 is positioned above to the plane 620 of the coronary artery ostium 612 during diastole, the distance D can be associated with an identifier to indicate such (e.g., a negative sign (−)).

FIG. 7 illustrates an example of the aortic valve of FIG. 6 with the prosthetic valve 702 implanted therein. In particular, the prosthetic valve 702 is expanded to an implanted/deployed state at the aortic valve. As shown, the native leaflet 604 is repositioned to a substantially straight and vertical position. Here, the native leaflet 604 and/or the prosthetic valve 702 at least partially blocks the coronary ostium 612.

In some embodiments, the techniques and systems discussed herein can evaluate one or more procedure/post-procedure images representing the anatomical features shown in FIG. 7 to identify anatomical features that are visible/represented in the one or more images, such as an aortic wall(s), the calcium deposit 614, the coronary artery 610, the prosthetic valve 710, and/or other anatomical features that are visible/represented. Based on identifying anatomical features that are visible/represented in the one or more procedure/post-procedure images, the techniques and systems can determine characteristics/positions for the visible/represented anatomical features (and/or hidden/non-represented anatomical features), with the positioning being represented with one or more dimensions.

FIG. 7 shows some example dimensions (which can represent/identify positions of anatomical features) that can be determined for one or more procedure/post-procedure images, including: a distance/dimension H between the plane 620 of the coronary artery ostium 612 and the upper end of the calcium deposit 614 (e.g., a plane 704 of the upper end of the calcium deposit 614); a distance/dimension I between the frame of the prosthetic valve 702 and the center of the coronary ostium 612; a distance/dimension J between the plane 704 of the upper end of the calcium deposit 614 and the sino-tubular junction (STJ) plane 706; and/or a distance/dimension K between the plane 704 of the upper end of the calcium deposit 614 and an upper end 708 of the prosthetic valve 702.

In some embodiments, if the upper end of the calcium deposit 614 is positioned below to the plane 620 of the coronary artery ostium 612 after deployment of the prosthetic valve 702, the distance H can be associated with an identifier to indicate such (e.g., a positive sign (+)). Further, if the upper end of the calcium deposit 614 is positioned above to the plane 620 of the coronary artery ostium 612 after deployment of the prosthetic valve 702, as shown in FIG. 7, the distance H can be associated with an identifier to indicate such (e.g., a negative sign (−)). Further, in some embodiments, when the prosthetic valve 702 is implanted, a position of an upper end/tip of the native leaflet 604 approximates a position of a center of the coronary ostium 612.

In some embodiments, the techniques and systems discussed herein can determine one or more additional dimensions to represent/identify the anatomical features with the prosthetic valve 702 implanted based on one or more of the dimensions discussed above in reference to FIGS. 6 and/or 7, including, for example: a distance/dimension K-H between the upper end 708 of the prosthetic valve 702 and the plane 620 of the coronary artery ostium 612 (i.e., the distance K plus the distance H); a distance/dimension J-K between the STJ plane 706 and the upper end 708 of the prosthetic valve 702 (i.e., the distance J minus the distance K); a distance/dimension J-E between the STJ plane 706 and the upper end/tip 616 of the native leaflet 604 (i.e., the distance J minus the distance E); a distance/dimension K-E between the upper end 708 of the prosthetic valve 702 and the upper end 616 of the native leaflet 604 (i.e., the distance K minus the distance E); and/or a distance/dimension E-H between the upper end 616 of the native leaflet 604 and the plane 620 of the coronary artery ostium 612 (i.e., the distance E plus the distance H).

In some embodiments, the techniques and systems discussed herein can use one or more of the dimensions discussed above to determine an amount of access into the coronary artery 620. For example, the distances K-H, K-E, and/or J-E can indicate an amount of space available to access the coronary artery 610 above/through the prosthetic valve 702 and/or above the native leaflet 604. In other words, the distances K-H, K-E, and/or J-E can be indicative of how much the prosthetic valve 702 and/or the native leaflet 604 are obstructing the coronary ostium 612 to the coronary artery 610. Such information can be useful to determine if a procedure can be performed with access through the coronary artery 610 due to the implantation of the prosthetic valve 702. With the prosthetic valve 702 implanted in the aortic valve (as shown in FIG. 7), the amount of access to the coronary artery 610 is reduced, in comparison to the aortic valve without the prosthetic valve (as shown in FIG. 6). Although distances K-H, K-E, and/or J-E are discussed in examples, one or more other dimensions can be used in determining an amount of space available to access to the coronary artery 610.

Although some example dimensions are discussed in reference to FIGS. 6 and 7, other dimensions can additionally or alternatively be determined. In some embodiments, the techniques and systems discussed herein can use one or more algorithms to determine a distance/dimension associated with an anatomical feature, such as an algorithm that converts a number of pixels or a distance between pixels in an image to a distance/dimension for an anatomical feature.

Example Flow Diagrams

Figure 8A:
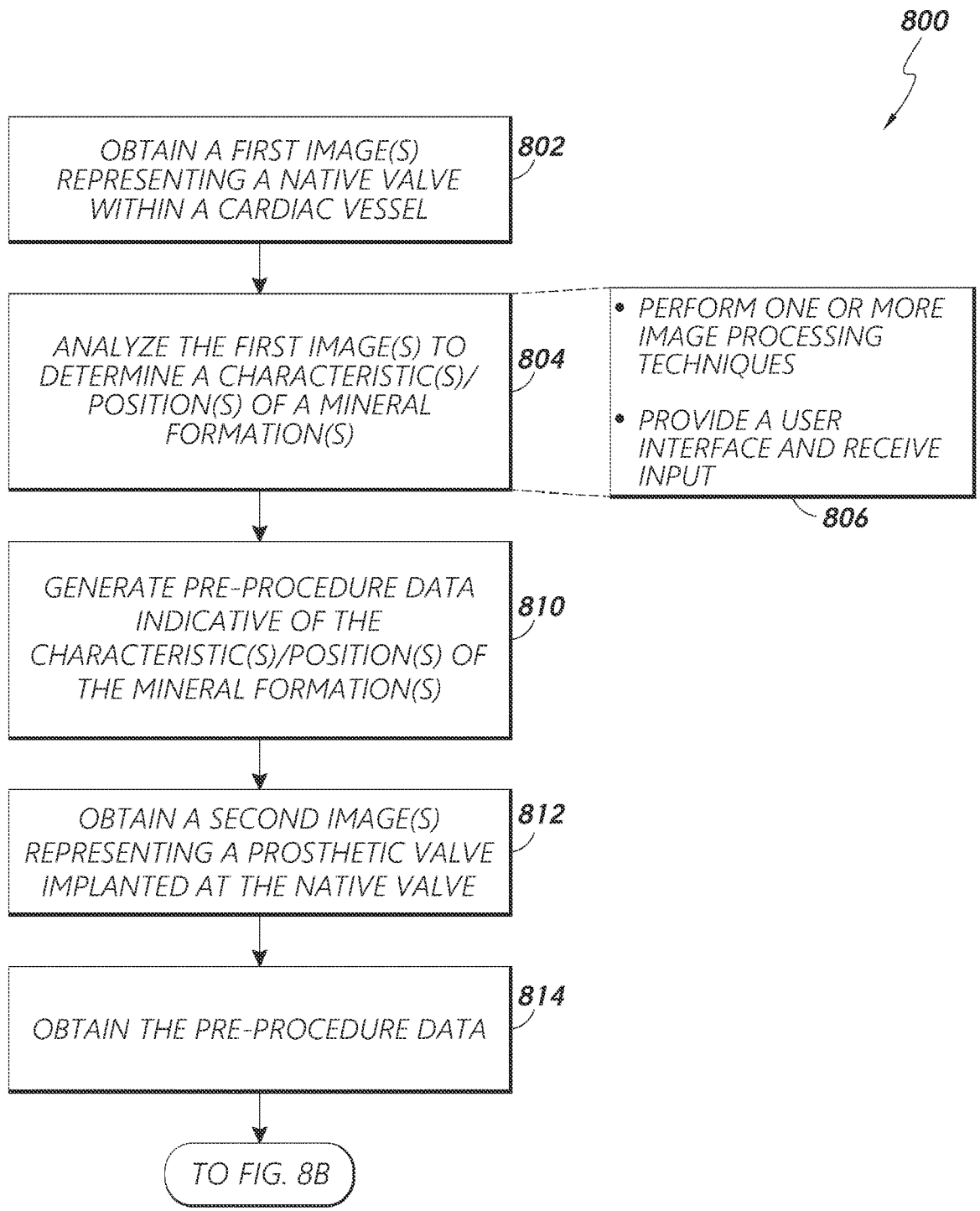
FIGS. 8A-8B illustrate an example flow diagram of a process for analyzing one or more images to determine a position/characteristic of an anatomical feature in accordance with one or more embodiments.
Figure 8B:
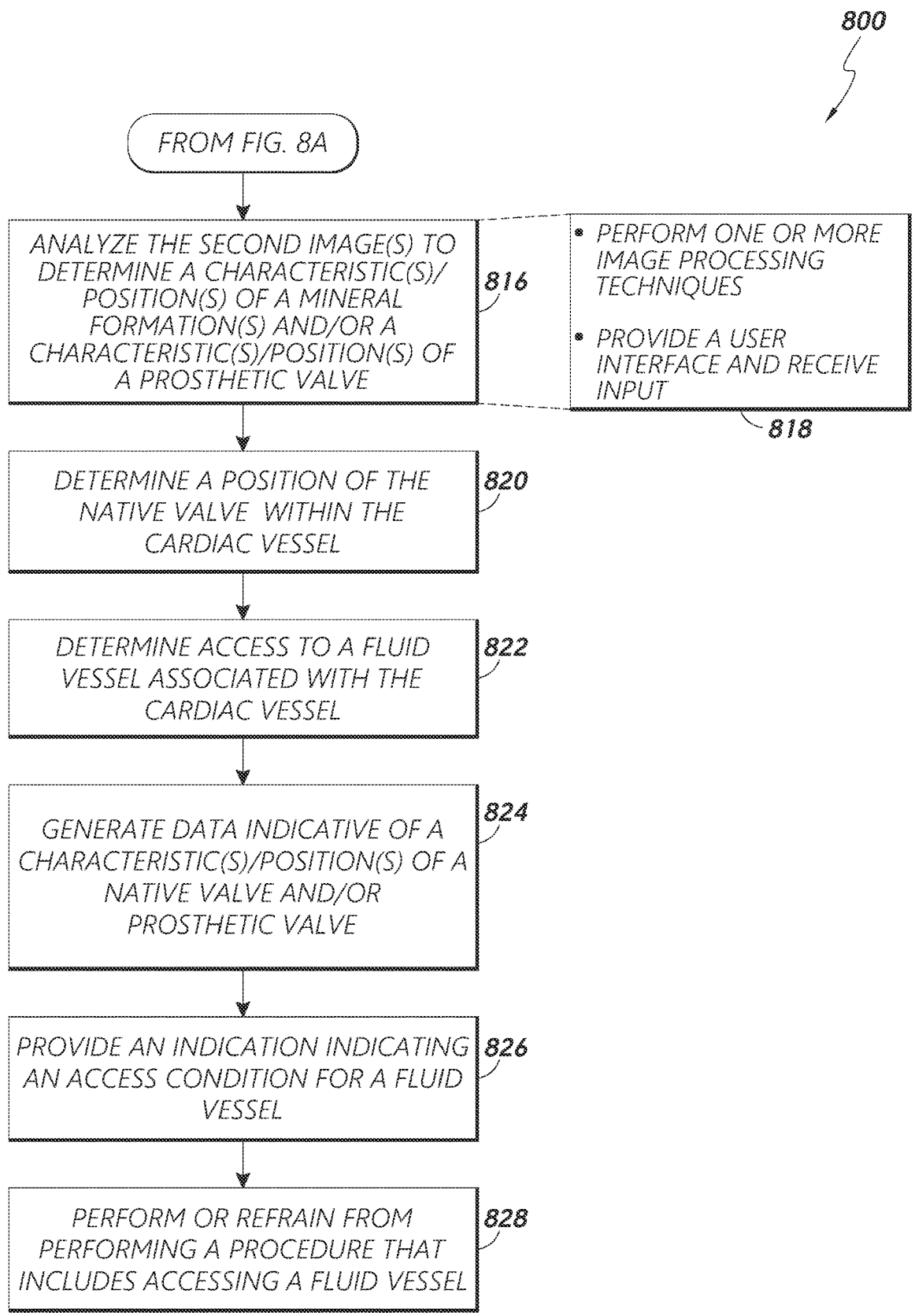
Figure 9:
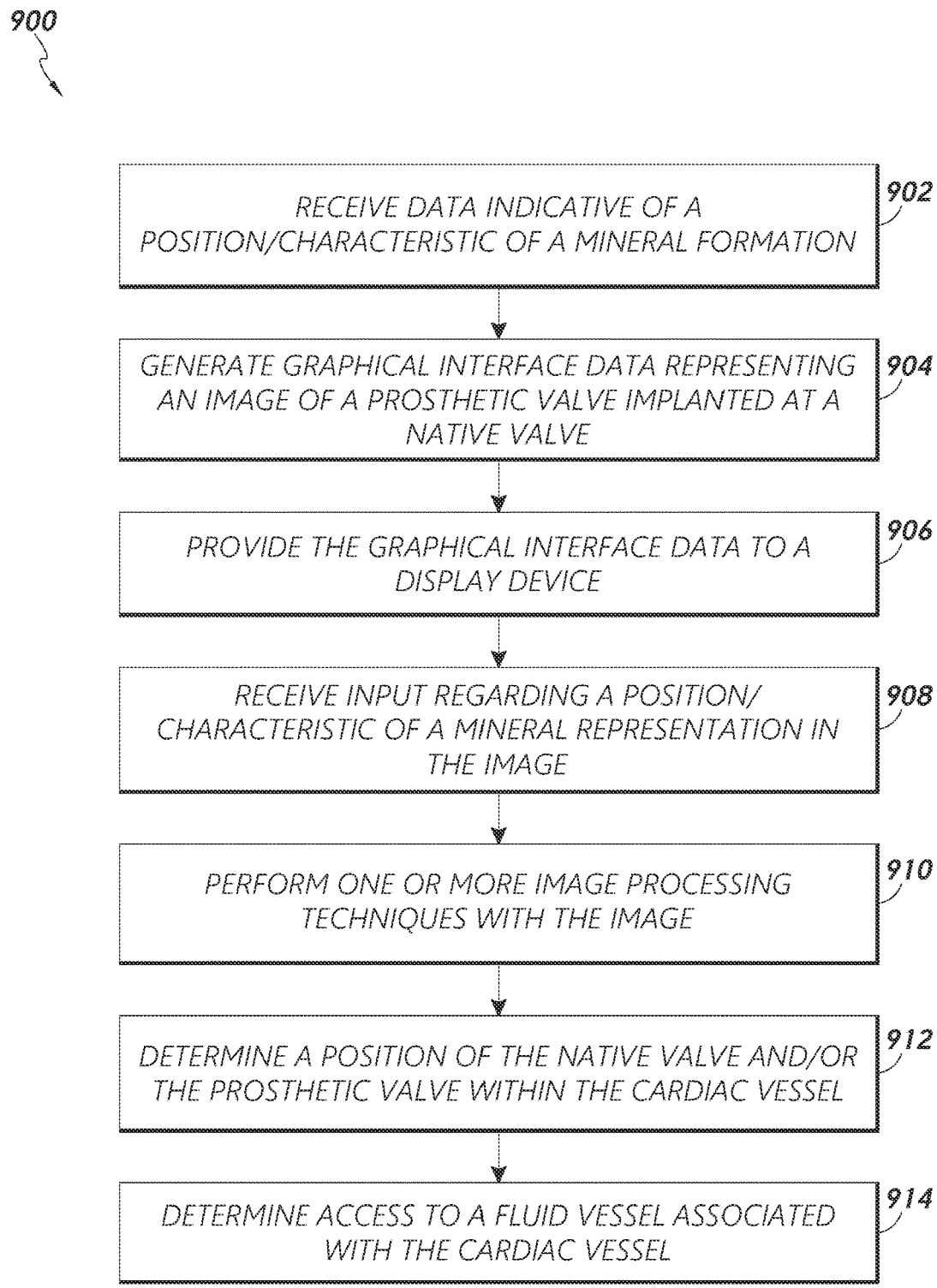
FIG. 9 illustrates an example flow diagram of a process for providing an interface to determine a position/characteristic of an anatomical feature in accordance with one or more embodiments.

FIGS. 8A, 8B, and 9 illustrate example flow diagrams of processes for performing one or more techniques discussed herein. The various blocks associated with the processes can be performed by one or more devices/systems, users, and so on. For example, one or more of the blocks can be performed by control circuitry of the computing system 506 and/or the imaging device 502, and/or performed by a physician, a technician, and/or any other user.

FIGS. 8A-8B illustrate an example flow diagram of a process 804 for analyzing one or more images to determine a position/characteristic of an anatomical feature in accordance with one or more embodiments. In FIG. 8A, at block 802, the process 800 can include obtaining one or more first images representing a native valve within a cardiac vessel. In some embodiments, control circuitry of a device/system can receive one or more pre-procedure images from an imaging device. The one or more pre-procedure images can include data representing a cardiac vessel, such as the aortic valve within the aortic annulus region. Further, in some embodiments, a user can obtain/receive one or more pre-procedure images from an imaging device, a computing system, and/or another device/system.

At block 804, the process 800 can include analyzing the one or more first images to determine one or more characteristics/positions of one or more mineral formations. In examples, a characteristic of a mineral formation can include a size/shape/dimension of the mineral formation. Further, in examples, a position of a mineral formation can include a position of the mineral formation relative to an anatomical feature, such as a tip/end or another portion of a native leaflet, the coronary artery, the aortic wall, a coordinate system/space, and so on.

In some embodiments, as illustrated in block 806, control circuitry can perform one or more image processing techniques with one or more pre-procedure images to determine one or more characteristics/positions of one or more mineral formations. For example, the one or more image processing techniques can include detection that seeks to identify one or more image features within an image (e.g., edges, corners, blobs, ridges, and so on), tracking that seeks to track one or more image features across images/frames, and/or classification that seeks to classify the one or more image features into one or more categories. In examples, the one or more image processing techniques can use one or more models, such as a machine-trained model, user-trained model, or another model that has been trained to classify image features (e.g., such as image features that represent mineral formations). In some embodiments, control circuitry can determine any of the dimensions discussed in reference to FIGS. 6 and 7.

Further, in some embodiments, is also illustrated in block 806, control circuitry can provide a user interface to a user and/or receive input regarding one or more characteristics/positions of one or more mineral formations. For example, the control circuitry can generate user interface data representing a user interface that includes a pre-procedure image and/or send the user interface data to a display device for display of the user interface, including the pre-procedure image. A user can view the pre-procedure image through the interface and provide input identifying a position of a mineral formation. In one example, the user can designate a representation/location in an image as representing a mineral formation. In another example, a user can designate a first point/location on an image and a second point/location on the image and provide input requesting that a distance be calculated between the first point/location and the second point/location. The first point/location and/or the second point/location can be on or within proximity to a mineral representation. As such, the distance can be indicative of a position of the mineral formation relative to another feature. In some embodiments, a user can select various points/locations on an image to designate (and/or cause the control circuitry to determine) any of the dimensions discussed in reference to FIGS. 6 and 7.

In some embodiments, control circuitry and/or a user can identify a tip/end of a native leaflet based on coapt leaflets (i.e., leaflets that are contacting or are in proximity to each other). For example, the control circuitry and/or the user can identify a region in an image that is associated with a particular shading/color/size that is typically associated with coapt leaflets. The control circuitry and/or the user can designate the region of coapt leaflets as a tip/end of a native leaflet. In examples, the control circuitry and/or the user can determine a position of a mineral formation relative to the tip/end of the native leaflet, such as a distance between the position of the mineral formation and the tip/end of the native leaflet.

At block 810, the process 800 can include generating pre-procedure data indicative of the one or more characteristics/positions of the one or more mineral formations. In some embodiments, control circuitry can generate pre-procedure data indicative of one or more characteristics/positions of one or more mineral formations based on a characteristic/position determined/identified at block 804. Once generated, the pre-procedure data can be stored in a datastore, such as a datastore associated with the control circuitry and/or located over a network.

At block 812, the process 800 can include obtaining one or more second images representing a prosthetic valve implanted at the native valve. In some embodiments, control circuitry can receive one or more procedure/post-procedure images from an imaging device. The one or more procedure/post-procedure images can include data representing a prosthetic valve in a cardiac vessel, such as a prosthetic aortic valve deployed in the aortic valve. Further, in some embodiments, a user can obtain/receive one or more procedure/post-procedure images from an imaging device, a computing system, and/or another device/system.

At block 814, the process 800 can include obtaining the pre-procedure data. In some embodiments, control circuitry can retrieve pre-procedure data from a datastore, which can be located over a network in some cases. In examples, pre-procedure data can be indicative of one or more characteristics/positions of one or more mineral formations before implantation of a prosthetic valve. Further, in some embodiments, a user can obtain/receive pre-procedure data.

In FIG. 8B, at block 816, the process 800 can include analyzing the one or more second images to determine one or more characteristics/positions of one or more mineral formations and/or one or more characteristics/positions of a prosthetic valve.

In some embodiments, as illustrated in block 818, control circuitry can perform one or more image processing techniques with one or more procedure/post-procedure images to determine one or more characteristics/positions of one or more mineral formations, which can include one or more of the techniques discussed above in reference to block 806. In examples, the control circuitry can obtain pre-procedure data indicative of a characteristic of a mineral formation/pre-procedure mineral representation, such as a size/shape/color of the mineral formation and/or a size/shape/color of a visual representation representing the mineral formation in a pre-procedure image. The control circuitry can use the pre-procedure data to identify a mineral representation in a procedure/post-procedure image that has one or more similar characteristics (e.g., that satisfy one or more similarity thresholds) to the mineral formation/mineral representation in the pre-procedure image.

Further, in some embodiments, control circuitry can perform one or more image processing techniques with one or more procedure/post-procedure images to determine one or more characteristics/positions of a prosthetic valve. For example, the control circuitry can identify one or more representations in a post-procedure image as corresponding to one or more elements of a prosthetic valve if the one or more representations are positioned along a substantially vertical plane/axis, are connected together via one or more connecting representations, have characteristic of typical prosthetic valves, etc. In examples, the control circuitry can reference a library of prosthetic valve data to identify characteristics of prosthetic valves, such as a size/shape of a typical frame or another feature of a prosthetic valve.

Further, in some embodiments, as also illustrated in block 818, control circuitry can provide a user interface to a user and/or receive input regarding one or more characteristics/positions of one or more mineral formations and/or a prosthetic valve. For example, the control circuitry can generate user interface data representing a user interface that includes a procedure/post-procedure image and/or send the user interface data to a display device for display of the user interface. A user can view the procedure/post-procedure image through the interface and provide input identifying a position of a mineral formation and/or a position of a prosthetic valve, similar to one or more of the techniques discussed above in reference to block 806. In examples, the user interface can view a pre-procedure image and/or information regarding a mineral formation in a pre-procedure image to assist the user in identifying a mineral formation in a procedure/post-procedure image.

At block 820, the process 800 can include determining a position of the native valve within the cardiac vessel. In some embodiments, control circuitry and/or a user can determine a position of a native valve/leaflet within the cardiac vessel based on the position of a mineral formation on a native leaflet before implantation of the prosthetic valve (which can be indicated in pre-procedure data) and/or a position of the mineral formation within the cardiac vessel after implantation of the prosthetic valve. In examples, a position/orientation of a native leaflet can be estimated based on a position of one or more mineral formations and/or a position of a prosthetic frame. For example, if multiple mineral formations and/or frame elements of a prosthetic valve are identified in a substantially vertical plane/axis, a native leaflet can be estimated to be substantially parallel to the vertical plane/axis and/or within a distance to the vertical plane/axis.

At block 822, the process 800 can include determining access to a fluid vessel associated with the cardiac vessel. For example, control circuitry and/or a user can determine an amount of access to a fluid vessel associated with the cardiac vessel based on a position of a native valve within the cardiac vessel after implantation of a prosthetic valve, a position of a prosthetic valve within the cardiac vessel, and so on. The amount of access can be indicative of available space above the native leaflet and/or the prosthetic valve and/or through a portion of the prosthetic valve that is above the native leaflet. In some embodiments, the control circuitry can determine one or more of the dimensions illustrated in FIGS. 6 and/or 7, and use the one or more dimensions to determine an amount of available space, such as between a tip/end of a native leaflet and a portion of the aortic wall that is substantially above the tip/end of the native leaflet, between an upper end of a prosthetic valve and a portion of the aortic wall that is substantially above the end of the prosthetic valve, and so on.

Further, in some embodiments, control circuitry can provide a user interface with a procedure/post-procedure image and a user can provide input to select an upper end of a mineral formation and select a portion of the aortic wall. The user can provide input requesting that a distance be calculated between the upper end of the mineral formation and the portion of the aortic wall. The control circuitry can determine such distance and use the distance, as well as any other distances, to determine an amount of access space.

At block 824, the process 800 can include generating data indicative of one or more characteristics/positions of a native valve and/or a prosthetic valve. For example, control circuitry can generate data indicative of one or more characteristics/positions of a native valve/leaflet and/or a prosthetic valve after implantation of the prosthetic valve within the cardiac vessel. In some embodiments, the data can also be indicative of an amount of access to a fluid vessel, such as a dimension indicating an amount of access to the fluid vessel. The control circuitry can store the data in a datastore.

At block 826, the process 800 can include providing an indication indicating an access condition for a fluid vessel, such as a coronary access condition. In some examples, an indication can be provided indicating a risk/risk level associated with performing a procedure that includes accessing a fluid vessel (e.g., high/medium/low risk that there is blockage to the coronary artery due to implantation of a prosthetic valve and/or a position of a native leaflet). For instance, the indication can indicate that access to the coronary artery is completely blocked, partially block, open (e.g., not blocked), and so on. An indication can be based on and/or indicate an amount of access to a fluid vessel. In some embodiments, an indication is provided to a user via a display or other output device, such as a visual/audio representation. However, the indication can be provided in other manners. In some embodiments, a patient can be associated with an indication indicating an access condition to a fluid vessel.

At block 828, the process 800 can include performing or refraining from performing a procedure that includes accessing a fluid vessel. In some embodiments, the process 800 can include determining that an amount of access to a coronary artery is less than a threshold and/or that a risk/risk level is a particular value (e.g., a relatively high risk of blockage to the coronary artery) and, based on such determination, refraining from performing a procedure that includes accessing the coronary artery. Alternatively or additionally, the process 800 can include determining that an amount of access to a coronary artery is greater than a threshold and/or that a risk/risk level is a particular value (e.g., a relatively low risk of blockage to the coronary artery) and, based on such determination, performing a procedure that includes accessing the coronary artery.

One or more of blocks 802-828 can be performed at various times. In some embodiments, one or more of blocks 802-810 can be performed before a prosthetic valve has been implanted and one or more of blocks 812-828 can be performed after a prosthetic valve has been implanted. Further, in some embodiments, one or more of blocks 802-810 can be performed after a prosthetic valve has been implanted. For example, one or more pre-procedure images, taken before the prosthetic valve was implanted, can be analyzed after the prosthetic valve has been implanted. However, blocks 802-828 can be performed at other times and/or in any order.

FIG. 9 illustrates an example flow diagram of a process 900 for providing an interface to determine a position/characteristic of an anatomical feature in accordance with one or more embodiments. At block 902, the process 900 can include receiving data indicative of a position/characteristic of a mineral formation. For example, control circuitry can retrieve pre-procedure data from a datastore. In some embodiments, pre-procedure data can be indicative of one or more characteristics/positions of one or more mineral formations before implantation of a prosthetic valve, such as a position of a mineral formation relative to an end/tip of a native leaflet.

At block 904, the process 900 can include generating graphical interface data representing an image of a prosthetic valve implanted at a native valve. For example, control circuitry can generate user interface data representing a user interface that includes a procedure/post-procedure image of a prosthetic valve implanted at a native valve.

At block 906, the process 900 can include providing the graphical interface data to a display device. For example, control circuitry can send graphical interface data to a display device for display of a user interface, including a procedure/post-procedure image. In some embodiments, the display device is a component of a computing system in which the control circuitry is located, while in other embodiments the display device is a component of another computing system.

At block 908, the process 900 can include receiving input regarding a position/characteristic of a mineral representation in the image. For example, control circuitry can receive input via a user interface regarding a position/characteristic of a mineral representation depicted in a procedure/post-procedure image, such as input identifying a position of a mineral formation, a dimension associated with the mineral formation, etc.

At block 910, the process 900 can include performing one or more image processing techniques with the image. For example, control circuitry can perform one or more image processing techniques with a procedure/post-procedure image to determine that a mineral representation in the image represents a mineral formation on a native leaflet. In examples, the one or more image processing techniques can use data indicative of one or more characteristics of the mineral formation.

At block 912, the process 900 can include determining a position of the native valve and/or the prosthetic valve within the cardiac vessel. For example, control circuitry can determine a position of a native valve/leaflet within the cardiac vessel based on input received at block 908, image processing performed at block 910, and/or pre-procedure data indicative of a position/characteristic of a mineral formation.

At block 914, the process 900 can include determining access to a fluid vessel associated with the cardiac vessel. For example, control circuitry can determine an amount of access to a coronary artery based on a position of a native valve/leaflet and/or a position of at least a portion of the prosthetic valve within the cardiac vessel.

Example Images

Figure 10:
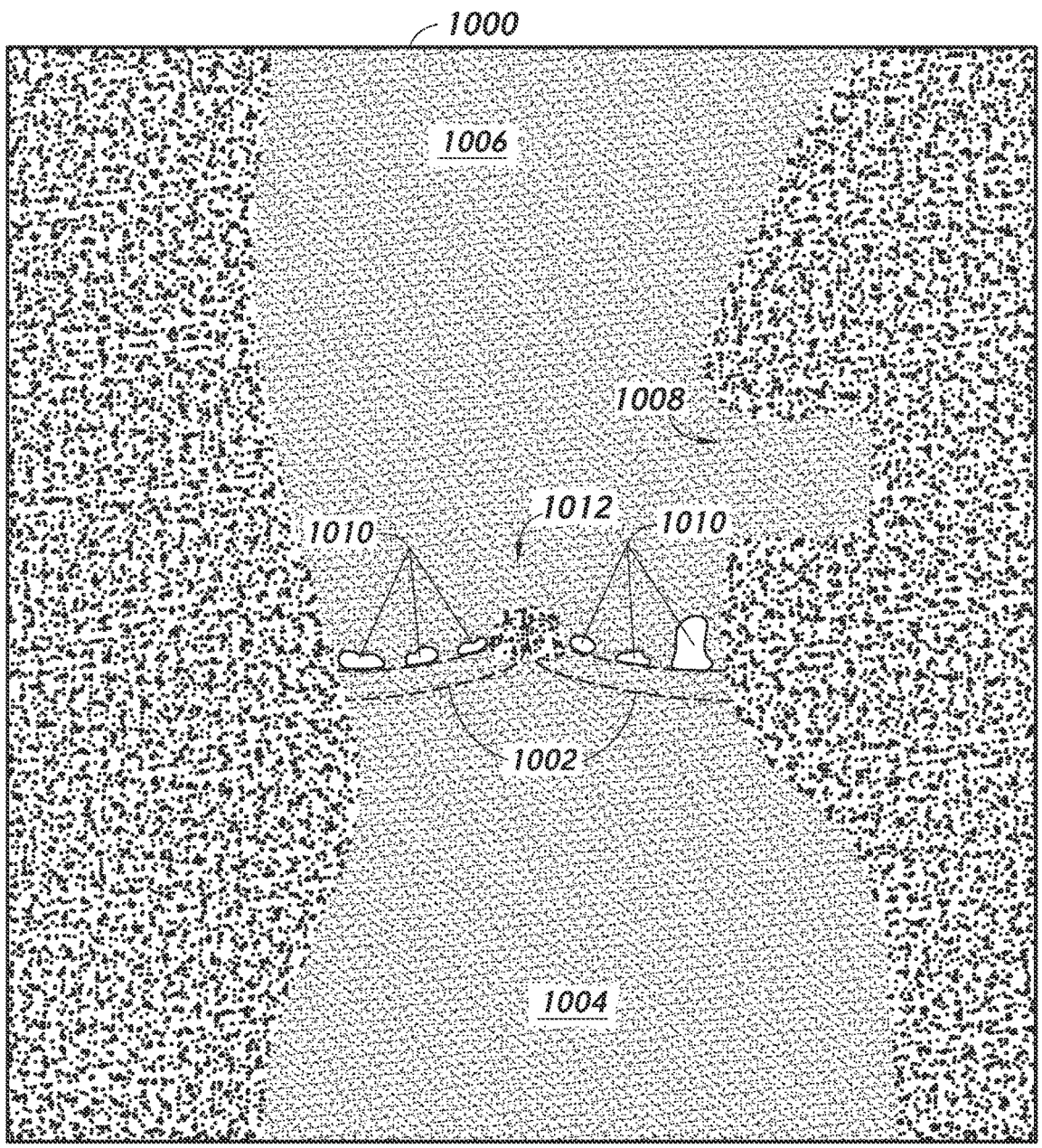
FIG. 10 illustrates an example image of a cardiac vessel before implantation of a prosthetic valve in accordance with one or more embodiments.
Figure 11:
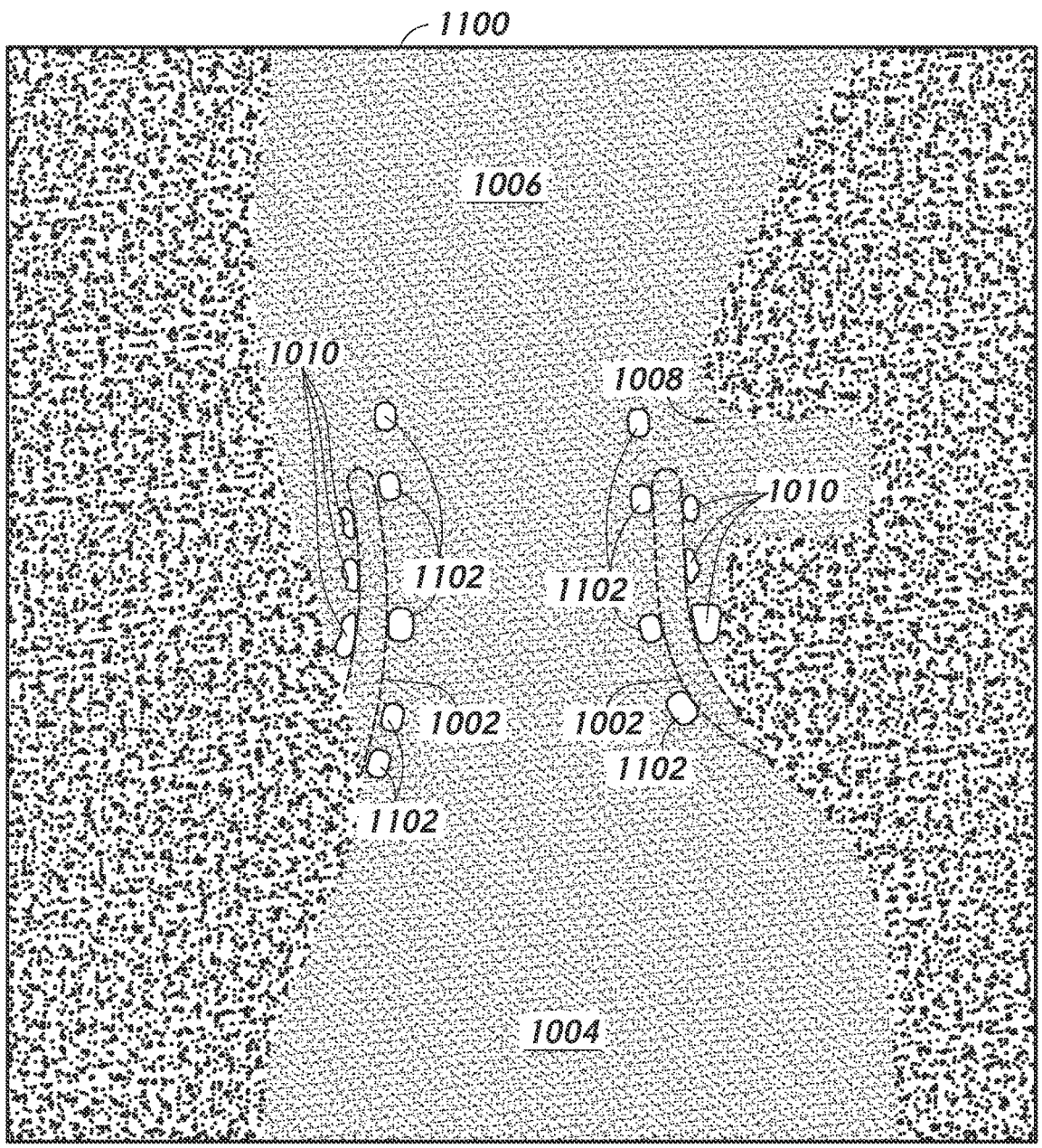
FIG. 11 illustrates an example image of a cardiac vessel after implantation of a prosthetic valve in accordance with one or more embodiments.

FIGS. 10 and 11 illustrates an example pre-procedure image 1000 and post-procedure image 1100, respectively, that can be generated by an imaging device in accordance with one or more embodiments. In these examples, the images 1000 and 1100 represent CT or x-ray images depicting various anatomical features within the aortic valve region. For example, the images 1000 and 1100 depict the aortic valve 1002 located between the left ventricle 1004 and the aorta 1006 and depict the coronary artery 1008 located above the aortic valve 1002. FIG. 10 depicts the aortic valve region in a pre-procedure state without the prosthetic valve 1102, while FIG. 11 depicts the aortic valve region with a prosthetic valve 1102 implanted to replace the aortic valve 1002. Although the native leaflets of the aortic valve 1002 may not generally be visible/represented within CT or x-ray images, for ease of illustration the native leaflets of the aortic valve 1002 are shown in FIGS. 10 and 11 with dotted lines.

In these examples, the aortic valve 102 includes calcium deposits 1010, which can appear as white representations within the images 1000 and 1100 (e.g., lighter regions). The calcium deposits 1010 can include particular characteristics/positions that can enable the calcium deposits 1010 to be detected by an imaging device. For example, the calcium deposits 1010 can each have a size that satisfies a size/thickness threshold associated with detection by an imaging device. Although the calcium deposits 1010 are illustrated as being attached to a top of the native leaflets of the aortic valve 1002 in these examples, the calcium deposits 1010 can be attached/embedded below and/or within the native leaflets.

As shown in FIG. 10, the pre-procedure image 1000 also includes a slightly darker region 1012 depicting coapt leaflets. The coapt leaflets can include particular characteristics/positions that can enable the coapt leaflets to be detected by an imaging device. For example, since the coapt leaflets include two or more native leaflets that may contact or come within proximity to each other, creating a substantially thicker region than the native leaflets alone, the coapt leaflets can satisfy a size/thickness threshold associated with detection by an imaging device. The region 1012 can generally represent the ends/tips of the native leaflets of the aortic valve 1002. As such, although the native leaflets of the aortic valve 1002 may not generally be visible/represented within the pre-procedure image 1000, the tip/end of a native leaflet of the aortic valve 1000 may be visible/represented (e.g., with the darker region 1012) when the native leaflet is coapting with another leaflet.

In some embodiments, the systems and techniques discussed herein can analyze the pre-procedure image 1000 of FIG. 10 to identify features that are visible/represented within the pre-procedure image 1000 and/or determine one or more characteristics/positions of visible/represented and/or hidden/non-represented features. For example, the systems and techniques can identify the calcium deposits 1010, the region 1012 representing the tips/ends of the native leaflets of the aortic valve 1002, aortic walls, the coronary artery 1008, and/or other anatomical features. The systems and techniques can also determine characteristics regarding such features, such as a position of a feature, a size/shape of a feature, etc. In some embodiments, the systems and techniques can use the positions of the calcium deposits 1010 to estimate a position of the native leaflets of the aortic valve 1002. For example, a position of the native leaflets of the aortic valve 1002 can be estimated to be below/above/at the calcium deposits 1010. Data regarding the characteristics/positions of the calcium deposits 1010 and/or the estimated characteristics/positions of the native leaflets of the aortic valve 1002 (and/or other information) can be stored as pre-procedure data.

As noted above, FIG. 11 illustrates the post-procedure image 1100 depicting the aortic valve region with the prosthetic valve 1102 implanted to replace the aortic valve 1002. Here, the native leaflets of the aortic valve 1002 are pressed toward the aortic wall and the coronary artery 1008 due to the radially outward force applied by the prosthetic valve 1002. Since a frame of the prosthetic valve 1102 can generally have a size/thickness that satisfies a size/thickness threshold associated with detection by an imaging device, the frame of the prosthetic valve 1102 can be detected by the imaging device and represented in the post-procedure image 1100. As shown in FIG. 11, a frame of the prosthetic valve 1102 is depicted with white representations (e.g., representing multiple frame elements/portions).

In some embodiments, the systems and techniques discussed herein can analyze the post-procedure image 1100 of FIG. 11 to identify features that are visible/represented within the post-procedure image 1100 and/or determine one or more characteristics/positions of visible/represented and/or hidden/non-represented features. For example, the systems and techniques can identify the calcium deposits 1010, the aortic walls, the coronary artery 1008, the prosthetic valve 1102 frame elements, and/or other anatomical features. The systems and techniques can also determine characteristics regarding such features, such as a position of a feature, a size/shape of a feature, etc. In some embodiments, the systems and techniques can use the positions of the calcium deposits 1010 in the pre-procedure image 1000 to estimate a position of the native leaflets of the aortic valve 1002 and/or access to the coronary artery 1008 (e.g., an amount of access to the coronary artery 1008). Data regarding the characteristics/positions of the calcium deposits 1010, the estimated characteristics/positions of the native leaflets of the aortic valve 1002, and/or the estimated access (and/or other information) can be stored as post-procedure data. In some embodiments, the systems and techniques discussed herein can map the potential of sinus sequestration.

ADDITIONAL FEATURES AND EMBODIMENTS

The above description of embodiments of the disclosure is not intended to be exhaustive or to limit the disclosure to the precise form disclosed above. While specific embodiments, and examples, are described above for illustrative purposes, various equivalent modifications are possible within the scope of the disclosure, as those skilled in the relevant art will recognize. For example, while processes or blocks are presented in a given order, alternative embodiments can perform routines having steps, or employ systems having blocks, in a different order, and some processes or blocks may be deleted, moved, added, subdivided, combined, and/or modified. Each of these processes or blocks can be implemented in a variety of different ways. Also, while processes or blocks are at times shown as being performed in series, these processes or blocks can instead be performed in parallel or can be performed at different times.

Certain terms of location are used herein with respect to the various disclosed embodiments. Although certain spatially relative terms, such as "outer," "inner," "upper," "lower," "below," "above," "vertical," "horizontal," "top," "bottom," and similar terms are used herein to describe a spatial relationship of one device/element or anatomical structure relative to another device/element or anatomical structure, it is understood that these terms are used herein for ease of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure can represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

It should be understood that certain ordinal terms (e.g., "first" or "second") can be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather can generally distinguish the element from another element having a similar or identical name (but for use of the ordinal term). In addition, as used herein, indefinite articles ("a" and "an") can indicate "one or more" rather than "one." Further, an operation performed "based on" a condition or event can also be performed based on one or more other conditions or events not explicitly recited. In some contexts, description of an operation or event as occurring or being performed "based on," or "based at least in part on," a stated event or condition can be interpreted as being triggered by or performed in response to the stated event or condition.

With respect to the various methods and processes disclosed herein, although certain orders of operations or steps are illustrated and/or described, it should be understood that the various steps and operations shown and described can be performed in any suitable or desirable temporal order. Furthermore, any of the illustrated and/or described operations or steps can be omitted from any given method or process, and the illustrated/described methods and processes can include additional operations or steps not explicitly illustrated or described.

It should be appreciated that in the above description of embodiments, various features are sometimes grouped together in a single embodiment, figure, or description thereof for the purpose of streamlining the disclosure and aiding in the understanding of one or more of the various aspects of the disclosure. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure should not be limited by the particular embodiments described above but should be determined only by a fair reading of the claims that follow.

Unless the context clearly requires otherwise, throughout the description and the claims, the terms "comprise," "comprising," "have," "having," "include," "including," and the like are to be construed in an open and inclusive sense, as opposed to a closed, exclusive, or exhaustive sense; that is to say, in the sense of "including, but not limited to."

The word "coupled", as generally used herein, refers to two or more elements that can be physically, mechanically, and/or electrically connected or otherwise associated, whether directly or indirectly (e.g., via one or more intermediate elements, components, and/or devices. Additionally, the words "herein," "above," "below," and words of similar import, when used in this application, shall refer to this application as a whole, including any disclosure incorporated by reference, and not to any particular portions of the present disclosure. Where the context permits, words in present disclosure using the singular or plural number can also include the plural or singular number, respectively.

The word "or" in reference to a list of two or more items, that word covers all of the following interpretations of the word: any of the items in the list, all of the items in the list, and any combination of the items in the list. Furthermore, as used herein, the term "and/or" used between elements (e.g., between the last two of a list of elements) means any one or more of the referenced/related elements. For example, the phrase "A, B, and/or C" means "A," "B," "C," "A and B," "A and C," "B and C," or "A, B, and C."

As may be used herein, the terms "substantially" and "approximately" provide an industry-accepted tolerance for its corresponding term and/or relativity between items. For some industries, an industry-accepted tolerance is less than one percent, while for other industries, the industry-accepted tolerance can be 10 percent or more. Other examples of industry-accepted tolerances range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances can be more or less than a percentage level (e.g., dimension tolerance of less than approximately +/−1%). Some relativity between items can range from a difference of less than a percentage level to a few percent. Other relativity between items can range from a difference of a few percent to magnitude of differences.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks can also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

The one or more embodiments are used herein to illustrate one or more aspects, one or more features, one or more concepts, and/or one or more examples. A physical embodiment of an apparatus, an article of manufacture, a machine, and/or of a process can include one or more of the aspects, features, concepts, examples, etc. described with reference to one or more of the embodiments discussed herein. Further, from figure to figure, the embodiments can incorporate the same or similarly named functions, steps, modules, etc. that can use the same, related, or unrelated reference numbers. The relevant features, elements, functions, operations, modules, etc. can be the same or similar functions or can be unrelated.

What is claimed is:
1. A method for determining a position of a native leaflet, the method comprising:
 obtaining a pre-procedure image representing a native valve within a cardiac vessel;

analyzing the pre-procedure image to determine a position of a mineral deposit on a native leaflet of the native valve;

based at least in part on the analysis of the pre-procedure image, identifying a coapt position at which the native leaflet contacts or comes into close proximity with a second native leaflet within the cardiac vessel;

based at least in part on the coapt position, determining an edge of the native leaflet;

determining a distance between the edge of the native leaflet and the mineral deposit;

obtaining, by control circuitry, a post-procedure image representing a prosthetic valve implanted at the native valve;

analyzing the post-procedure image to identify a position of the mineral deposit within the cardiac vessel;

identifying a position of a portion of the prosthetic valve within the cardiac vessel; and based at least in part on the distance between the edge of the native leaflet and the mineral deposit and the position of the portion of the prosthetic valve within the cardiac vessel, determining, by the control circuitry, a position of the edge of the native leaflet within the cardiac vessel.

2. The method of claim 1, wherein the native valve comprises the aortic valve and the cardiac vessel comprises the aorta.

3. The method of claim 1 further comprising:
based at least in part on the position of the edge of the native leaflet within the cardiac vessel, determining access to a fluid vessel associated with the cardiac vessel.

4. The method of claim 1, wherein the analyzing the pre-procedure image to identify the position of the mineral deposit on the native leaflet comprises:
generating user interface data representing the pre-procedure image;
providing the user interface data to a display device;
receiving input regarding the mineral deposit; and
identifying the position of the mineral deposit based at least in part on the input.

5. The method of claim 1, wherein the analyzing the pre-procedure image to identify the position of the mineral deposit on the native leaflet comprises:
performing one or more image processing techniques with the pre-procedure image to identify the position of the mineral deposit on the native leaflet.

6. The method of claim 1, wherein the identifying the coapt position includes detecting a region within a cardiac-vessel area of the pre-procedure image that has a characteristic that is different than another region of the cardiac-vessel area, the cardiac-vessel area representing the cardiac vessel.

7. A computing system comprising:
control circuitry; and
memory communicatively coupled to the control circuitry and storing executable instructions that, when executed by the control circuitry, cause the control circuitry to perform operations comprising:
receiving data indicative of a position of a mineral formation on a native leaflet of a native valve within a cardiac vessel;
generating graphical interface data representing an image of a prosthetic valve implanted at the native valve;
receiving input regarding a position of a mineral representation in the image;
analyzing the image to identify a position of a portion of the prosthetic valve within the cardiac vessel; and
based at least in part on the input and the position of the portion of the prosthetic valve, determining a position of the native leaflet within the cardiac vessel.

8. The computing system of claim 7, wherein the image comprises at least one of a computed tomography image or an x-ray image of the cardiac vessel.

9. The computing system of claim 7, wherein the native valve comprises the aortic valve and the cardiac vessel comprises the aorta.

10. The computing system of claim 7, wherein the operations further comprise:
based at least in part on the position of the native leaflet within the cardiac vessel, determining an amount of access to a coronary artery.

11. The computing system of claim 7, wherein the data is indicative of a position of the mineral formation relative to an end of the native leaflet, and the determining the position of the native leaflet within the cardiac vessel is based at least in part on the position of the mineral formation relative to the end of the native leaflet.

12. The computing system of claim 7, wherein the data indicates one or more characteristics of the mineral formation, and the operations further comprise:
based at least in part on the data, performing one or more image processing techniques with the image to determine that the mineral representation in the image represents the mineral formation on the native leaflet.

13. The computing system of claim 7, wherein the determining the position of the native leaflet includes analyzing the image based at least in part on the input.

14. The computing system of claim 7, wherein the operations further comprise:
analyzing a pre-procedure image to identify a coapt position at which a native leaflet contacts or comes into close proximity with a second native leaflet within the cardiac vessel;
based at least in part on the coapt position, determining an edge of the native leaflet; and
determining a distance between the edge of the native leaflet and the mineral formation;
wherein the determining the position of the native leaflet within the cardiac vessel is based at least in part on the distance between the edge of the native leaflet and the mineral formation.

15. A method comprising:
analyzing a pre-procedure image to identify a coapt position at which a native leaflet contacts or comes into close proximity with a second native leaflet within a cardiac vessel;
based at least in part on the coapt position, identifying an edge of the native leaflet;
determining a distance between the edge of the native leaflet and a mineral formation;
obtaining, by control circuitry, a post-procedure image representing a prosthetic valve implanted at a native valve within the cardiac vessel;
analyzing the post-procedure image to identify a position of the mineral formation within the cardiac vessel; and
based at least in part on the position of the mineral formation and the distance between the edge of the native leaflet and the mineral formation, determining a position of the native leaflet within the cardiac vessel.

16. The method of claim 15, further comprising:
based at least in part on the position of the native leaflet within the cardiac vessel, determining an amount of access to a fluid vessel associated with the cardiac vessel.

17. The method of claim 16, further comprising:
identifying a position of at least a portion of the prosthetic valve within the cardiac vessel;
wherein the determining the amount of access to the fluid vessel is based at least in part on the position of at least the portion of the prosthetic valve within the cardiac vessel.

18. The method of claim 15, wherein the analyzing the post-procedure image to identify the position of the mineral formation within the cardiac vessel comprises:
performing one or more image processing techniques with the post-procedure image to identify the position of the mineral formation within the cardiac vessel.

19. The method of claim 15, wherein the identifying the coapt position includes detecting a region within a cardiac-vessel area of the pre-procedure image that has a characteristic that is different another region of the cardiac-vessel area, the cardiac-vessel area representing the cardiac vessel.

* * * * *